US010433902B2

(12) United States Patent
Cadouri

(10) Patent No.: US 10,433,902 B2
(45) Date of Patent: Oct. 8, 2019

(54) CURRENT CONTROL METHODS AND SYSTEMS

(71) Applicant: Medtronic Ardian Luxembourg S.a.r.l., Luxembourg (LU)

(72) Inventor: Hadar Cadouri, Sunnyvale, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 426 days.

(21) Appl. No.: 14/089,305

(22) Filed: Nov. 25, 2013

(65) Prior Publication Data
US 2015/0112321 A1 Apr. 23, 2015

Related U.S. Application Data

(60) Provisional application No. 61/894,572, filed on Oct. 23, 2013.

(51) Int. Cl.
*A61B 18/18* (2006.01)
*A61B 18/14* (2006.01)
(Continued)

(52) U.S. Cl.
CPC ...... *A61B 18/1492* (2013.01); *A61B 18/1206* (2013.01); *A61B 2018/00005* (2013.01);
(Continued)

(58) Field of Classification Search
CPC ............ A61B 18/1206; A61B 18/1492; A61B 2018/00005; A61B 2018/00404;
(Continued)

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| EP | 0768841 | 4/1997 |
| EP | 1169976 | 1/2002 |

(Continued)

OTHER PUBLICATIONS

European Search Report for European Application No. 13159256, dated Oct. 17, 2013, 6 pages.
(Continued)

*Primary Examiner* — Michael F Peffley
*Assistant Examiner* — Amanda L Zink
(74) *Attorney, Agent, or Firm* — Medtronic Vascular, Inc. IP Legal Department

(57) ABSTRACT

Apparatus, systems, and methods of controlling energy delivered to electrodes used in electrically and/or thermally induced neuromodulation are provided to improve neuromodulation. In particular, a catheter treatment device having a control algorithm that regulates current or current density delivered to an electrode is provided. The electrode may maintain a known and consistent electrode contact surface area with the vessel. The control algorithm controls energy delivery to provide consistent current or current density to the treatment site, even though the tissue impedance Z may vary from patient to patient and vessel to vessel, and despite changes in impedance of the treatment site during the course of the treatment. The controlled delivery of energy can be used to control and maintain placement of the zone of thermal treatment and reduce undesirable energy delivery to unwanted locations near the treatment site.

13 Claims, 15 Drawing Sheets

(51) Int. Cl.
*A61B 18/12* (2006.01)
*A61B 18/00* (2006.01)

(52) U.S. Cl.
CPC .......... *A61B 2018/0072* (2013.01); *A61B 2018/00404* (2013.01); *A61B 2018/00434* (2013.01); *A61B 2018/00511* (2013.01); *A61B 2018/00577* (2013.01); *A61B 2018/00648* (2013.01); *A61B 2018/00738* (2013.01); *A61B 2018/00779* (2013.01); *A61B 2018/00791* (2013.01); *A61B 2018/00827* (2013.01); *A61B 2018/00875* (2013.01); *A61B 2018/00886* (2013.01); *A61B 2018/00892* (2013.01); *A61B 2018/00898* (2013.01)

(58) Field of Classification Search
CPC ........... A61B 2018/00434; A61B 2018/00511; A61B 2018/00577; A61B 2018/00648; A61B 2018/0072; A61B 2018/00738; A61B 2018/00779; A61B 2018/00791; A61B 2018/00827; A61B 2018/008
See application file for complete search history.

(56) References Cited

U.S. PATENT DOCUMENTS

| | | | |
|---|---|---|---|
| 4,709,698 | A | 12/1987 | Johnston et al. |
| 4,727,874 | A * | 3/1988 | Bowers ............... H03F 1/52 330/207 A |
| 4,764,504 | A | 8/1988 | Johnson et al. |
| 4,890,623 | A | 1/1990 | Cook et al. |
| 4,976,711 | A | 12/1990 | Parins et al. |
| 5,300,068 | A | 4/1994 | Rosar et al. |
| 5,358,514 | A | 10/1994 | Schulman et al. |
| 5,366,443 | A | 11/1994 | Eggers et al. |
| 5,368,591 | A | 11/1994 | Lennox et al. |
| 5,423,744 | A | 6/1995 | Gencheff et al. |
| 5,423,808 | A | 6/1995 | Edwards et al. |
| 5,423,810 | A | 6/1995 | Goble et al. |
| 5,425,364 | A | 6/1995 | Imran |
| 5,437,662 | A | 8/1995 | Nardella |
| 5,437,664 | A | 8/1995 | Cohen et al. |
| 5,456,682 | A * | 10/1995 | Edwards ............... A61B 18/00 600/549 |
| 5,462,545 | A * | 10/1995 | Wang ............... A61B 18/1492 600/373 |
| 5,472,443 | A | 12/1995 | Cordis et al. |
| 5,484,400 | A | 1/1996 | Edwards et al. |
| 5,496,312 | A | 3/1996 | Klicek |
| 5,540,681 | A | 7/1996 | Strul et al. |
| 5,540,684 | A | 7/1996 | Hassler, Jr. |
| 5,542,916 | A * | 8/1996 | Hirsch ............... A61B 18/00 604/164.08 |
| 5,562,721 | A | 10/1996 | Marchlinski et al. |
| 5,571,147 | A | 11/1996 | Sluijter et al. |
| 5,573,533 | A | 11/1996 | Strul |
| 5,584,830 | A | 12/1996 | Ladd et al. |
| 5,588,964 | A | 12/1996 | Imran et al. |
| 5,599,345 | A | 2/1997 | Edwards et al. |
| 5,626,576 | A | 5/1997 | Janssen |
| 5,658,619 | A | 8/1997 | Kirschner et al. |
| 5,672,174 | A | 9/1997 | Gough et al. |
| 5,688,266 | A | 11/1997 | Edwards et al. |
| 5,697,882 | A | 12/1997 | Eggers et al. |
| 5,697,925 | A | 12/1997 | Taylor |
| 5,700,282 | A | 12/1997 | Zabara |
| 5,702,386 | A | 12/1997 | Stern et al. |
| 5,707,400 | A | 1/1998 | Terry, Jr. et al. |
| 5,735,846 | A | 4/1998 | Panescu et al. |
| 5,755,715 | A | 5/1998 | Stern et al. |
| 5,769,847 | A | 6/1998 | Panescu et al. |
| 5,772,590 | A | 6/1998 | Webster, Jr. |
| 5,810,802 | A | 9/1998 | Panescu et al. |
| 5,817,092 | A | 10/1998 | Behl |
| 5,817,093 | A | 10/1998 | Williamson, IV et al. |
| 5,860,974 | A | 1/1999 | Abele |
| 5,865,787 | A | 2/1999 | Shapland et al. |
| 5,868,737 | A | 2/1999 | Taylor et al. |
| 5,871,481 | A | 2/1999 | Kannenberg et al. |
| 5,893,885 | A | 4/1999 | Webster et al. |
| 5,906,614 | A | 5/1999 | Stern et al. |
| 5,907,589 | A | 5/1999 | Koifman et al. |
| 5,944,710 | A | 8/1999 | Dev et al. |
| 5,954,719 | A | 9/1999 | Chen et al. |
| 5,976,128 | A | 11/1999 | Schilling et al. |
| 5,983,141 | A | 11/1999 | Sluijter et al. |
| 6,004,269 | A | 12/1999 | Crowley et al. |
| 6,009,877 | A | 1/2000 | Edwards |
| 6,023,638 | A | 2/2000 | Swanson |
| 6,024,740 | A | 2/2000 | Lesh et al. |
| 6,036,687 | A | 3/2000 | Laufer et al. |
| 6,039,731 | A | 3/2000 | Taylor et al. |
| 6,066,134 | A | 5/2000 | Eggers et al. |
| 6,080,149 | A | 6/2000 | Huang et al. |
| 6,091,995 | A | 7/2000 | Ingle et al. |
| 6,099,524 | A | 8/2000 | Lipson et al. |
| 6,113,592 | A * | 9/2000 | Taylor ............... A61B 5/0422 600/374 |
| 6,117,101 | A | 9/2000 | Diederich et al. |
| 6,117,131 | A * | 9/2000 | Taylor ............... A61B 5/0422 600/374 |
| 6,123,702 | A | 9/2000 | Swanson et al. |
| 6,135,999 | A | 10/2000 | Fanton et al. |
| 6,142,993 | A | 11/2000 | Whayne et al. |
| 6,149,620 | A | 11/2000 | Baker et al. |
| 6,161,048 | A | 12/2000 | Sluijter et al. |
| 6,183,468 | B1 | 2/2001 | Swanson et al. |
| 6,197,021 | B1 | 3/2001 | Panescu et al. |
| 6,210,403 | B1 | 4/2001 | Klicek |
| 6,212,426 | B1 | 4/2001 | Swanson |
| 6,217,573 | B1 | 4/2001 | Webster |
| 6,219,577 | B1 | 4/2001 | Brown, III et al. |
| 6,224,592 | B1 | 5/2001 | Eggers et al. |
| 6,238,387 | B1 | 5/2001 | Miller, III |
| 6,245,065 | B1 | 6/2001 | Panescu et al. |
| 6,246,912 | B1 | 6/2001 | Sluijter et al. |
| 6,273,886 | B1 | 8/2001 | Edwards et al. |
| 6,283,951 | B1 | 9/2001 | Flaherty et al. |
| 6,292,695 | B1 | 9/2001 | Webster, Jr. et al. |
| 6,293,941 | B1 | 9/2001 | Strul et al. |
| 6,314,325 | B1 | 11/2001 | Fitz |
| 6,322,558 | B1 | 11/2001 | Taylor et al. |
| 6,322,559 | B1 | 11/2001 | Daulton et al. |
| 6,358,246 | B1 | 3/2002 | Behl et al. |
| 6,366,808 | B1 | 4/2002 | Schroeppel et al. |
| 6,405,732 | B1 | 6/2002 | Edwards et al. |
| 6,413,255 | B1 | 7/2002 | Stern |
| 6,423,057 | B1 | 7/2002 | He et al. |
| 6,428,537 | B1 | 8/2002 | Swanson et al. |
| 6,451,015 | B1 | 9/2002 | Rittman, III et al. |
| 6,464,696 | B1 | 10/2002 | Oyama et al. |
| 6,488,678 | B2 | 12/2002 | Sherman |
| 6,488,679 | B1 | 12/2002 | Swanson et al. |
| 6,494,880 | B1 | 12/2002 | Swanson et al. |
| 6,500,172 | B1 | 12/2002 | Panescu et al. |
| 6,506,189 | B1 | 1/2003 | Rittman, III et al. |
| 6,508,815 | B1 * | 1/2003 | Strul ............... A61B 18/1206 606/34 |
| 6,511,476 | B2 | 1/2003 | Hareyama |
| 6,514,226 | B1 | 2/2003 | Levin et al. |
| 6,514,248 | B1 | 2/2003 | Eggers et al. |
| 6,522,926 | B1 | 2/2003 | Kieval et al. |
| 6,542,781 | B1 | 4/2003 | Koblish et al. |
| 6,546,270 | B1 * | 4/2003 | Goldin ............... A61B 18/12 600/374 |
| 6,558,378 | B2 | 5/2003 | Sherman et al. |
| 6,558,382 | B2 | 5/2003 | Jahns et al. |
| 6,562,034 | B2 | 5/2003 | Edwards et al. |
| 6,616,624 | B1 | 9/2003 | Kieval |
| 6,622,731 | B2 | 9/2003 | Daniel et al. |
| 6,635,054 | B2 | 10/2003 | Fjield et al. |
| 6,635,057 | B2 | 10/2003 | Harano et al. |
| 6,640,120 | B1 | 10/2003 | Swanson et al. |

(56) References Cited

U.S. PATENT DOCUMENTS

| | | |
|---|---|---|
| 6,648,883 B2 | 11/2003 | Francischelli et al. |
| 6,666,862 B2 | 12/2003 | Jain et al. |
| 6,679,269 B2 | 1/2004 | Swanson |
| 6,682,527 B2 | 1/2004 | Strul |
| 6,685,648 B2 | 2/2004 | Flaherty et al. |
| 6,685,700 B2 | 2/2004 | Behl et al. |
| 6,711,444 B2 | 3/2004 | Koblish |
| 6,730,079 B2 | 5/2004 | Lovewell |
| 6,733,498 B2 | 5/2004 | Paton et al. |
| 6,736,835 B2 | 5/2004 | Pellegrino et al. |
| 6,752,804 B2 | 6/2004 | Simpson et al. |
| 6,752,805 B2 | 6/2004 | Maguire et al. |
| 6,761,716 B2 | 7/2004 | Kadhiresan et al. |
| 6,796,981 B2 | 9/2004 | Wham et al. |
| 6,845,267 B2 | 1/2005 | Harrison et al. |
| 6,849,073 B2 | 2/2005 | Hoey et al. |
| 6,850,801 B2 | 2/2005 | Kieval et al. |
| 6,855,141 B2 | 2/2005 | Lovewell |
| 6,855,142 B2 | 2/2005 | Harano et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto |
| 6,936,047 B2 | 8/2005 | Nasab et al. |
| 6,939,346 B2 | 9/2005 | Kannenberg et al. |
| 6,949,097 B2 | 9/2005 | Stewart et al. |
| 6,955,675 B2 | 10/2005 | Jain |
| 6,989,010 B2 | 1/2006 | Francischelli et al. |
| 7,001,379 B2 | 2/2006 | Behl et al. |
| 7,001,381 B2 | 2/2006 | Harano et al. |
| 7,008,417 B2 | 3/2006 | Eick |
| 7,025,764 B2 | 4/2006 | Paton et al. |
| 7,029,470 B2 | 4/2006 | Francischelli et al. |
| 7,066,933 B2 | 6/2006 | Hagg |
| 7,076,399 B2 | 7/2006 | Godara |
| 7,104,985 B2 | 9/2006 | Martinelli |
| 7,108,694 B2 | 9/2006 | Miura et al. |
| 7,131,445 B2 | 11/2006 | Amoah |
| 7,137,980 B2 | 11/2006 | Buysse et al. |
| 7,149,574 B2 | 12/2006 | Yun et al. |
| 7,162,303 B2 | 1/2007 | Levin et al. |
| 7,169,144 B2 | 1/2007 | Hoey et al. |
| 7,221,979 B2 | 5/2007 | Zhou et al. |
| 7,226,447 B2 | 6/2007 | Uchida et al. |
| 7,247,155 B2 | 7/2007 | Hoey et al. |
| 7,250,048 B2 | 7/2007 | Francischelli et al. |
| 7,258,688 B1 | 8/2007 | Shah et al. |
| 7,364,578 B2 | 4/2008 | Francischelli et al. |
| 7,367,972 B2 | 5/2008 | Francischelli et al. |
| 7,381,200 B2 | 6/2008 | Katoh et al. |
| 7,390,894 B2 | 6/2008 | Weinshilboum et al. |
| 7,429,261 B2 | 9/2008 | Kunis et al. |
| 7,533,002 B2 | 5/2009 | Godara |
| 7,582,084 B2 | 9/2009 | Swanson et al. |
| 7,596,469 B2 | 9/2009 | Godara |
| 7,617,005 B2 | 11/2009 | Demarais et al. |
| 7,620,451 B2 | 11/2009 | Demarais et al. |
| 7,647,115 B2 | 1/2010 | Levin et al. |
| 7,651,492 B2 | 1/2010 | Wham |
| 7,653,438 B2 | 1/2010 | Deem et al. |
| 7,717,909 B2 | 5/2010 | Strul et al. |
| 7,717,948 B2 | 5/2010 | Demarais et al. |
| 7,778,703 B2 | 8/2010 | Gross et al. |
| 7,792,589 B2 | 9/2010 | Levy, Jr. et al. |
| 7,799,020 B2 | 9/2010 | Shores et al. |
| 7,824,399 B2 | 11/2010 | Francischelli et al. |
| 7,837,679 B2 | 11/2010 | Biggs et al. |
| 7,842,076 B2 | 11/2010 | Zikorus et al. |
| 7,846,160 B2 | 12/2010 | Payne et al. |
| 7,887,534 B2 | 2/2011 | Hamel et al. |
| 7,901,400 B2 | 3/2011 | Wham et al. |
| 7,922,714 B2 | 4/2011 | Stevens-Wright |
| 7,927,328 B2 | 4/2011 | Orszulak et al. |
| 7,959,626 B2 | 6/2011 | Hong et al. |
| 7,963,962 B2 | 6/2011 | Thompson et al. |
| 7,972,328 B2 | 7/2011 | Wham et al. |
| 7,976,540 B2 | 7/2011 | Daw et al. |
| 8,048,070 B2 | 11/2011 | O'Brien et al. |
| 8,058,771 B2 | 11/2011 | Giordano et al. |
| 8,080,008 B2 | 12/2011 | Wham et al. |
| 8,086,315 B2 | 12/2011 | Schwartz et al. |
| 8,095,212 B2 | 1/2012 | Sato |
| 8,105,323 B2 | 1/2012 | Buysse et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,147,485 B2 | 4/2012 | Wham et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,801 B2 | 4/2012 | Goldberg et al. |
| 8,152,802 B2 | 4/2012 | Podhajsky et al. |
| 8,162,932 B2 | 4/2012 | Podhajsky et al. |
| 8,175,711 B2 | 5/2012 | Demarais et al. |
| 8,241,275 B2 | 8/2012 | Hong et al. |
| 8,273,084 B2 | 9/2012 | Kunis et al. |
| 8,340,763 B2 | 12/2012 | Levin et al. |
| 8,876,813 B2 | 11/2014 | Min et al. |
| 8,909,316 B2 | 12/2014 | Ng |
| 9,028,472 B2 | 5/2015 | Mathur et al. |
| 9,037,259 B2 | 5/2015 | Mathur |
| 9,155,589 B2 | 10/2015 | Jenson |
| 9,271,782 B2 * | 3/2016 | Paul .................. A61B 18/1492 |
| 9,561,070 B2 | 2/2017 | Brotz et al. |
| 2001/0014802 A1 | 8/2001 | Tu |
| 2002/0062123 A1 | 5/2002 | Mcclurken et al. |
| 2002/0091381 A1 | 7/2002 | Edwards |
| 2002/0091385 A1 | 7/2002 | Paton et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0004510 A1 | 1/2003 | Wham et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0065322 A1 | 4/2003 | Panescu et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0068304 A1 | 4/2004 | Paton et al. |
| 2004/0122420 A1 | 6/2004 | Amoah |
| 2004/0215186 A1 | 10/2004 | Cornelius et al. |
| 2005/0021020 A1 | 1/2005 | Blaha |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0203504 A1 * | 9/2005 | Wham ............... A61B 18/1442 606/34 |
| 2005/0228460 A1 | 10/2005 | Levin et al. |
| 2005/0283148 A1 | 12/2005 | Janssen et al. |
| 2006/0025765 A1 | 2/2006 | Landman et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0106375 A1 | 5/2006 | Werneth et al. |
| 2006/0142753 A1 | 6/2006 | Francischelli et al. |
| 2006/0161148 A1 | 7/2006 | Behnke |
| 2006/0206150 A1 | 9/2006 | Demarais et al. |
| 2006/0271111 A1 | 11/2006 | Demarais et al. |
| 2007/0016274 A1 | 1/2007 | Boveja et al. |
| 2007/0083193 A1 | 4/2007 | Werneth et al. |
| 2007/0083195 A1 | 4/2007 | Werneth et al. |
| 2007/0112342 A1 | 5/2007 | Pearson et al. |
| 2007/0129720 A1 | 6/2007 | Demarais et al. |
| 2007/0167943 A1 | 7/2007 | Janssen et al. |
| 2007/0173804 A1 * | 7/2007 | Wham ............... A61B 18/1206 606/34 |

(56) References Cited

U.S. PATENT DOCUMENTS

| | | |
|---|---|---|
| 2007/0173805 A1 | 7/2007 | Weinberg et al. |
| 2007/0203481 A1 | 8/2007 | Gregg et al. |
| 2007/0208333 A1 | 9/2007 | Uchida et al. |
| 2007/0265687 A1 | 11/2007 | Deem et al. |
| 2007/0270795 A1 | 11/2007 | Francischelli et al. |
| 2008/0015562 A1 | 1/2008 | Hong et al. |
| 2008/0071257 A1 | 3/2008 | Kotmel et al. |
| 2008/0077126 A1 | 3/2008 | Rashidi |
| 2008/0101356 A1 | 5/2008 | Babbar et al. |
| 2008/0147057 A1 | 6/2008 | Eisele |
| 2008/0188912 A1 | 8/2008 | Stone et al. |
| 2008/0188913 A1 | 8/2008 | Stone et al. |
| 2008/0228181 A1 | 9/2008 | Godara et al. |
| 2008/0262489 A1 | 10/2008 | Steinke |
| 2008/0281312 A1 | 11/2008 | Werneth et al. |
| 2008/0281322 A1* | 11/2008 | Sherman ............ A61B 18/1492 606/42 |
| 2008/0300589 A1 | 12/2008 | Paul et al. |
| 2008/0319513 A1 | 12/2008 | Pu et al. |
| 2009/0030477 A1 | 1/2009 | Jarrard |
| 2009/0036948 A1 | 2/2009 | Levin et al. |
| 2009/0182323 A1 | 7/2009 | Eder et al. |
| 2009/0182325 A1 | 7/2009 | Werneth et al. |
| 2009/0299365 A1 | 12/2009 | Stewart et al. |
| 2010/0137860 A1 | 6/2010 | Demarais et al. |
| 2010/0137952 A1 | 6/2010 | Demarais et al. |
| 2010/0179533 A1 | 7/2010 | Podhajsky |
| 2010/0179538 A1 | 7/2010 | Podhajsky |
| 2010/0191112 A1 | 7/2010 | Demarais et al. |
| 2010/0211063 A1 | 8/2010 | Wham et al. |
| 2010/0222851 A1 | 9/2010 | Deem et al. |
| 2010/0222854 A1 | 9/2010 | Demarais et al. |
| 2010/0228247 A1 | 9/2010 | Paul et al. |
| 2010/0324548 A1 | 12/2010 | Godara et al. |
| 2011/0077641 A1 | 3/2011 | Dunning |
| 2011/0087214 A1 | 4/2011 | Giordano et al. |
| 2011/0087217 A1 | 4/2011 | Yates et al. |
| 2011/0112400 A1 | 5/2011 | Emery et al. |
| 2011/0130755 A1 | 6/2011 | Bhushan et al. |
| 2011/0190755 A1 | 8/2011 | Mathur et al. |
| 2011/0230876 A1 | 9/2011 | Hong et al. |
| 2011/0270120 A1 | 11/2011 | McFarlin et al. |
| 2011/0270237 A1 | 11/2011 | Werneth et al. |
| 2011/0270247 A1 | 11/2011 | Sherman |
| 2012/0041502 A1 | 2/2012 | Schwartz et al. |
| 2012/0095461 A1 | 4/2012 | Herscher et al. |
| 2012/0101490 A1 | 4/2012 | Smith |
| 2012/0101538 A1 | 4/2012 | Ballakur et al. |
| 2012/0116383 A1 | 5/2012 | Mauch et al. |
| 2012/0130289 A1 | 5/2012 | Demarais et al. |
| 2012/0130345 A1 | 5/2012 | Levin et al. |
| 2012/0136346 A1 | 5/2012 | Condie et al. |
| 2012/0136348 A1 | 5/2012 | Condie et al. |
| 2012/0143097 A1 | 6/2012 | Pike, Jr. |
| 2012/0150169 A1 | 6/2012 | Zielinksi et al. |
| 2012/0172837 A1 | 7/2012 | Demarais et al. |
| 2012/0197243 A1 | 8/2012 | Sherman et al. |
| 2012/0310241 A1 | 12/2012 | Orszulak |
| 2013/0006228 A1 | 1/2013 | Johnson et al. |
| 2013/0006235 A1 | 1/2013 | Podhajsky et al. |
| 2013/0123778 A1 | 5/2013 | Richardson et al. |
| 2013/0165764 A1 | 6/2013 | Scheuermann et al. |
| 2013/0172878 A1 | 7/2013 | Smith |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0228614 A1 | 8/2014 | Stopek |
| 2014/0228829 A1 | 8/2014 | Schmitt et al. |
| 2014/0228858 A1 | 8/2014 | Stopek |
| 2014/0236137 A1 | 8/2014 | Tran et al. |
| 2014/0236138 A1 | 8/2014 | Tran et al. |
| 2014/0246465 A1 | 9/2014 | Peterson et al. |
| 2014/0249524 A1 | 9/2014 | Kocur |
| 2014/0257266 A1 | 9/2014 | Kasprzyk et al. |
| 2014/0266235 A1 | 9/2014 | Mathur |
| 2014/0275924 A1 | 9/2014 | Min et al. |
| 2014/0276124 A1 | 9/2014 | Cholette et al. |
| 2014/0276733 A1 | 9/2014 | VanScoy et al. |
| 2014/0276742 A1 | 9/2014 | Nabutovsky et al. |
| 2014/0276746 A1 | 9/2014 | Nabutovsky et al. |
| 2014/0276755 A1 | 9/2014 | Cao et al. |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0316400 A1 | 10/2014 | Blix et al. |
| 2014/0316496 A1 | 10/2014 | Masson et al. |
| 2014/0330266 A1 | 11/2014 | Thompson et al. |
| 2014/0336637 A1 | 11/2014 | Agrawal et al. |
| 2015/0005764 A1 | 1/2015 | Hanson et al. |
| 2015/0025524 A1 | 1/2015 | Nabutovsky |
| 2015/0245867 A1 | 9/2015 | Gross |
| 2016/0310201 A1 | 10/2016 | Brotz et al. |
| 2017/0007157 A1 | 1/2017 | Gross et al. |
| 2017/0007158 A1 | 1/2017 | Gross et al. |

FOREIGN PATENT DOCUMENTS

| | | |
|---|---|---|
| EP | 1366724 | 12/2003 |
| EP | 2460486 | 6/2012 |
| EP | 2747691 | 7/2014 |
| EP | 2797535 | 11/2014 |
| EP | 2914192 | 9/2015 |
| EP | 2967702 | 1/2016 |
| EP | 2967703 | 1/2016 |
| EP | 2967728 | 1/2016 |
| EP | 2967729 | 1/2016 |
| EP | 2967733 | 1/2016 |
| EP | 2968931 | 1/2016 |
| EP | 2991575 | 3/2016 |
| EP | 3158961 A1 | 4/2017 |
| JP | H08504531 | 5/1996 |
| JP | H1071037 | 3/1998 |
| JP | 2011505929 | 3/2011 |
| JP | 6122206 B2 | 4/2017 |
| WO | WO-9308757 | 5/1993 |
| WO | WO-1994007446 | 4/1994 |
| WO | WO1994007446 | 4/1994 |
| WO | WO-9410922 | 5/1994 |
| WO | WO-1995025472 | 9/1995 |
| WO | WO-1995031142 | 11/1995 |
| WO | WO1995031142 | 11/1995 |
| WO | WO-9600036 | 1/1996 |
| WO | WO-9639086 | 12/1996 |
| WO | WO-9704702 | 2/1997 |
| WO | WO-1997036548 | 10/1997 |
| WO | WO-9740882 | 11/1997 |
| WO | WO1998042403 | 10/1998 |
| WO | WO-1998042403 | 10/1998 |
| WO | WO-1999/00060 | 1/1999 |
| WO | WO-9900060 | 1/1999 |
| WO | WO-9960923 | 12/1999 |
| WO | WO-0015130 | 3/2000 |
| WO | WO-0122897 | 4/2001 |
| WO | WO-2001022897 | 4/2001 |
| WO | WO-2001070114 | 9/2001 |
| WO | WO2003022167 | 3/2003 |
| WO | WO-2003022167 | 3/2003 |
| WO | WO2003082080 | 10/2003 |
| WO | WO-2003082080 | 10/2003 |
| WO | WO-2005007001 | 1/2005 |
| WO | WO-2005030072 | 4/2005 |
| WO | WO-2005041748 | 5/2005 |
| WO | WO-2005051215 | 6/2005 |
| WO | WO-2005110528 | 11/2005 |
| WO | WO-2006041881 | 4/2006 |
| WO | WO-2006080982 | 8/2006 |
| WO | WO2006105121 | 10/2006 |
| WO | WO-2006105121 | 10/2006 |
| WO | WO-2007008954 | 1/2007 |
| WO | WO-2007067941 | 6/2007 |
| WO | WO-2007078997 | 7/2007 |
| WO | WO2007078997 | 7/2007 |

(56) References Cited

FOREIGN PATENT DOCUMENTS

| | | |
|---|---|---|
| WO | WO-2008003058 | 1/2008 |
| WO | WO2008049084 | 4/2008 |
| WO | WO-2008049084 | 4/2008 |
| WO | WO-2008101356 | 8/2008 |
| WO | WO-2010078175 | 7/2010 |
| WO | WO-2011017168 | 2/2011 |
| WO | WO-2011126580 | 10/2011 |
| WO | WO-2011144911 | 11/2011 |
| WO | WO-2012024631 | 2/2012 |
| WO | WO-2012054762 | 4/2012 |
| WO | WO-2012100095 | 7/2012 |
| WO | WO-2013030743 | 3/2013 |
| WO | WO-2013086461 | 6/2013 |
| WO | WO-2013101485 | 7/2013 |
| WO | WO-2014029355 | 2/2014 |
| WO | WO-2014059165 | 4/2014 |
| WO | WO-2014068577 | 5/2014 |
| WO | WO-2014/124241 | 8/2014 |
| WO | WO-2014/149550 | 9/2014 |
| WO | WO-2014/149552 | 9/2014 |
| WO | WO-2014/149553 | 9/2014 |
| WO | WO-2014/149690 | 9/2014 |
| WO | WO-2014150425 | 9/2014 |
| WO | WO-2014150432 | 9/2014 |
| WO | WO-2014150441 | 9/2014 |
| WO | WO-2014150455 | 9/2014 |
| WO | WO-2014/158713 | 10/2014 |
| WO | WO-2014163990 | 10/2014 |
| WO | WO-2014/179110 | 11/2014 |
| WO | WO-2014/182946 | 11/2014 |

OTHER PUBLICATIONS

Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul lntegr Comp Physiol 1997, vol. 272, 1997 the American Physiological Society, pp. 2034-2039.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

(56) References Cited

OTHER PUBLICATIONS

"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards ™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.

(56) References Cited

OTHER PUBLICATIONS

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.

Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.

(56) References Cited

OTHER PUBLICATIONS

Zheng et al., "Comparison of the temperature profile and pathological effect at unipolar, bipolar and phased radiofrequency current configurations," Journal of Interventional Cardiac Electrophysiology, 2001, pp. 401-410.
International Search Report and Written Opinion for International App. No. PCT/US2014/061805, dated Jan. 5, 2015, 11 pages.
U.S. Appl. No. 60/813,589, filed Dec. 29, 2005, 62 pp.
U.S. Appl. No. 60/852,787, filed Oct. 18, 2006, 112 pp.
Ureter, https://en.wikipedia.org/wiki/Ureter, Jun. 2016, 6 pp.
Search Report and Written Opinion dated Jan. 25, 2012 for PCT Application No. PCT/US2011/057740.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Opposition to European Patent No. 2465470, Granted Oct. 28, 2015, Date of Opposition Jul. 27, 2016, 34 pp.
Pieper, et al., "Design and Implementation of a New Computerized System for Intraoperative Cardiac Mapping" Journal of Applied Physiology, 1991, vol. 71 (4), pp. 1529-1539.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.
Messerli, Franz H. et al. "Renal Denervation for Resistant Hypertension: Dead or Alive?" Healio: Cardiology today's Intervention, May/Jun. 2014, 2 pages.

\* cited by examiner

CURRENT CONTROL METHODS AND SYSTEMS

RELATED APPLICATIONS

This application claims the benefit of U.S. Provisional Patent Application 61/894,572 filed Oct. 23, 2013. The disclosures of which are herein incorporated by reference in their entirety.

TECHNICAL FIELD

The present disclosure relates generally to the field of neuromodulation and associated systems and methods. More particularly, some embodiments relate to the methods and systems of controlling energy delivered to electrodes to improve neuromodulation.

BACKGROUND

The sympathetic nervous system (SNS) is primarily an involuntary bodily control system associated with stress responses. Fibers of the SNS innervate tissue and are present in almost every organ of the human body. The SNS can regulate characteristics such as pupil diameter, gut motility, and urinary output. Such regulation has adaptive utility in maintaining homeostasis or preparing the body for rapid responses to changes in environmental conditions. Chronic activation of the SNS, however, is a common maladaptive response that can drive the progression of many diseases. Excessive activation of the renal SNS, in particular, has been experimentally identified as a likely contributor to the complex pathophysiology of hypertension, volume overload states (such as heart failure), and progressive renal disease. Radiotracer dilution has demonstrated, for example, increased renal norepinephrine ("NE") spillover rates in patients with essential hypertension.

Cardio-renal sympathetic nerve hyperactivity can be pronounced in patients with heart failure. These patients often have an exaggerated NE overflow of plasma from the heart and kidneys. Heightened SNS activation commonly characterizes both chronic and end stage renal disease. In patients with end stage renal disease, NE plasma levels above the median are predictive of cardiovascular diseases and causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium (Na+) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate because of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal artery (e.g., via radiofrequency ablation) have been shown to reduce blood pressure in patients with treatment-resistant hypertension.

SUMMARY

Embodiments of the present technology are directed to apparatus, systems, and methods for controlling energy delivered to electrodes used in electrically and/or thermally induced neuromodulation (e.g., renal neuromodulation) to optimize neuromodulation despite changes in the impedance of the tissue being treated. In particular, embodiments of the present technology relate to apparatus, systems, and methods that incorporate a catheter treatment device having a control algorithm that regulates current or current density delivered to one or more neuromodulation electrodes.

Systems, methods and apparatus for controlling current delivered to an electrode for ablation procedures are disclosed. In some embodiments, the electrode is provided having a surface in contact with a vessel intima of a patient, and the process includes the operations of delivering energy to the electrode; measuring at least one of temperature, a voltage, and a current of the electrode; and adjusting the current delivered to the electrode based on at least one of the measured temperature, voltage, and current thereby controlling placement of a temperature zone.

In some embodiments, the operation can further include calculating a power level of the electrode based on the voltage and the current measured, and adjusting the current delivered to the electrode based on at least one of the measured temperature, measured voltage, measured current, and calculated power level. The operation may also include determining an area of the surface in contact with the vessel intima, determining a desired level of current density for a treatment, and adjusting an amount of current delivered to the electrode to achieve the desired current density. Adjusting the current can include, for example, adjusting the current density based on at least one of the measured temperature, voltage, and current.

In various embodiments, the surface area includes an active surface area and a passive surface area, and the operation further includes determining a desired level of current density for a treatment, determining an area of the active surface area in contact with the vessel wall and adjusting an amount of current delivered to the electrode to deliver the desired current density.

The operation of delivering energy to the electrode can include, for example, increasing or decreasing the current delivered to the electrode, to a determined current level, wherein the determined current level is determined based on at least one of a change in the temperature of the electrode, a change in impedance, and a calculated power of the electrode. Further, the current delivered to the electrode can be adjusted by limiting a rate of current change to a maximum change in current. A maximum increase in current can be determined a maximum current level, a maximum temperature, a maximum power, or a maximum change in impedance.

The system may be configured to terminate the energy delivered to the electrode based on a set amount of time, a predetermined temperature value, a predetermined current value, a predetermined integral of current over time value, and a predetermined impedance change value.

Current levels can be adjusted based on a rate of change in temperature of tissue at the electrode, and if temperature increases faster than a predetermined rate, reducing current delivered to the electrode. Accordingly, the process can be configured to adjust the current delivered to the electrode based on a rate of change in tissue impedance through a return path of the delivered energy, and if the impedance increases faster than a predetermined rate, reducing current delivered to the electrode.

In further embodiments, systems, methods and apparatus for controlling current delivered to an electrode having a surface in contact with a vessel intima, include the operations of determining a desired current density to deliver to target tissue adjacent the vessel intima to effectuate a treatment; determining an active surface area of the surface in contact with the vessel intima; calculating an amount of current to achieve the desired current density given the determined active surface area of the surface in contact with the vessel intima; and delivering the calculated amount of current to the electrode.

BRIEF DESCRIPTION OF THE DRAWINGS

The present invention, in accordance with one or more various embodiments, is described in detail with reference to the accompanying figures. The drawings are provided for purposes of illustration only and merely depict typical or example embodiments of the invention. These drawings are provided to facilitate the reader's understanding of the systems and methods described herein, and shall not be considered limiting of the breadth, scope, or applicability of the claimed invention.

Figure 1:
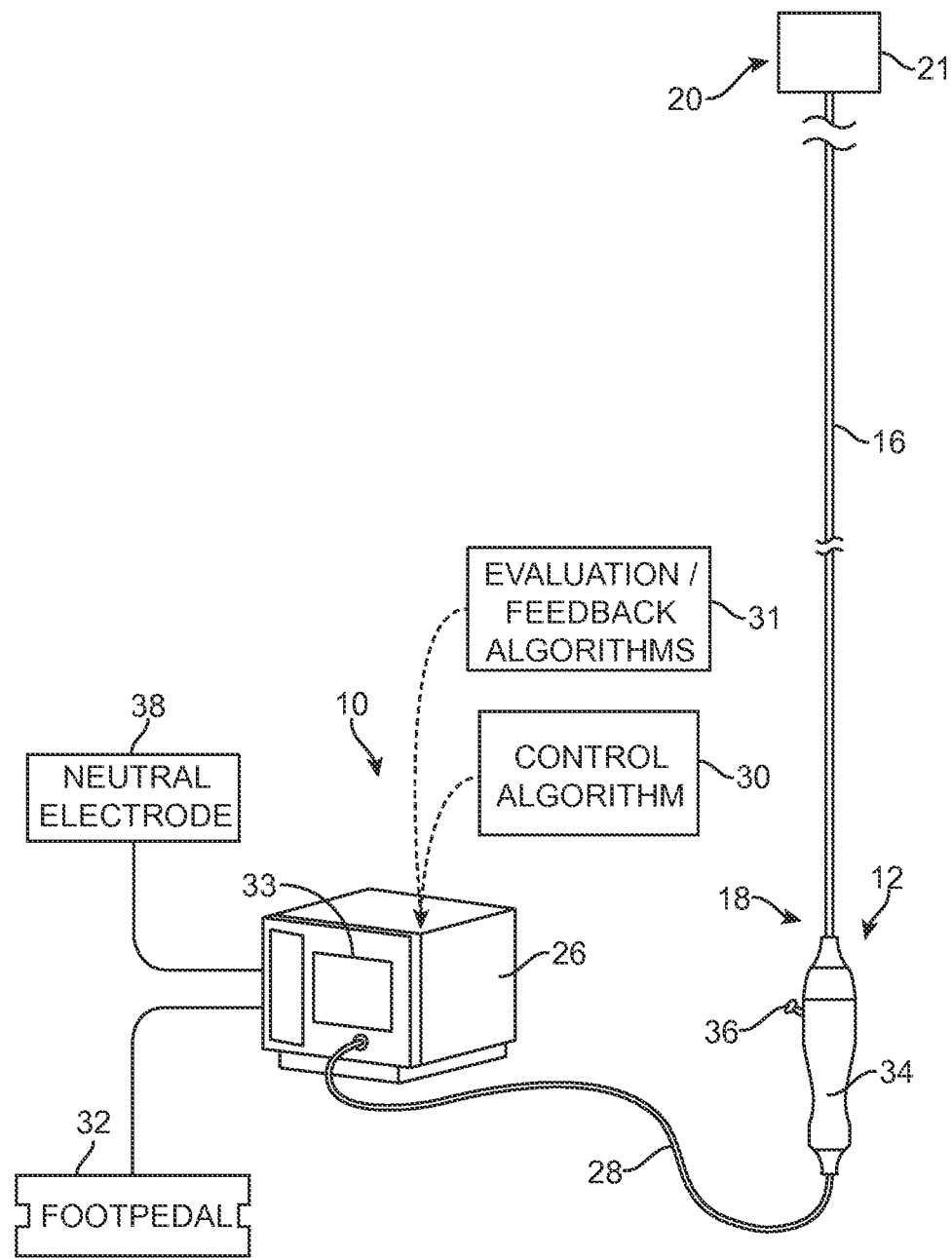
FIG. 1 illustrates a system 1 in accordance with an embodiment of the present technology.

The figures are not intended to be exhaustive or to limit the invention to the precise form disclosed. It should be understood that the invention can be practiced with modification and alteration, and that the invention be limited only by the claims and the equivalents thereof.

DESCRIPTION

Embodiments of the present technology are directed to apparatus, systems, and methods for controlling energy delivered to electrodes used in electrically and/or thermally induced neuromodulation (e.g., renal neuromodulation) to optimize neuromodulation despite changes or other variances in the impedance of the tissue being treated. In particular, embodiments of the present technology relate to apparatus, systems, and methods that incorporate a catheter treatment device having a control algorithm that regulates current or current density delivered to an electrode. The electrode is configured to deliver energy (e.g., electrical energy, radio frequency (RF) energy, pulsed electrical energy, or thermal energy) to a vessel wall (e.g., wall of a renal artery) after being advanced via a catheter along a percutaneous transluminal path (e.g., a femoral artery puncture, an iliac artery and aorta, a radial artery, or another suitable intravascular path). The electrode may maintain a known and consistent contact surface area with the vessel wall.

With the treatments disclosed herein for delivering therapy to target tissue, embodiments are provided that deliver energy to the target neural structures in a controlled manner. Various embodiments comprise a control algorithm that provides consistent current or current density regulation to control the amount of energy delivered in different cases, even though the tissue impedance Z may vary from patient to patient, vessel to vessel, or location to location within the vessel. The controlled delivery of energy can be used to allow the zone of thermal treatment to extend into the renal fascia while reducing undesirable energy delivery or unwanted adverse thermal effects to the vessel wall. A controlled delivery of energy may also result in a more consistent, predictable and efficient overall treatment.

Specific details of several embodiments of the present technology are described herein with reference to the accompanying figures. Other embodiments of the present technology can have configurations, components, or procedures different from those described herein. For example, other embodiments can include additional elements and features beyond those described herein or be without one or more of the elements and features shown and described herein.

I. Renal Neuromodulation

Renal neuromodulation is the partial or complete incapacitation or other effective disruption of nerves innervating the kidneys. In particular, renal neuromodulation comprises inhibiting, reducing, and/or blocking neural communication along efferent and/or afferent neural fibers innervating the kidneys. Such incapacitation can be for any length of time—minutes, hours, days, weeks, months, years, or permanent. Renal neuromodulation is expected to effectively treat several clinical conditions characterized by increased overall sympathetic activity, particularly conditions associated with central sympathetic overstimulation such as hypertension, heart failure, acute myocardial infarction, metabolic syndrome, insulin resistance, diabetes, left ventricular hypertrophy, chronic and end stage renal disease, cardio-renal syndrome, osteoporosis and conditions causing sudden deaths. The reduction of afferent neural signals contributes to the systemic reduction of sympathetic drive. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetes.

Various techniques can be used to partially or completely incapacitate neural pathways such as those innervating the kidney. The application of energy to tissue by the helical push wire electrode(s) can induce one or more desired thermal heating effects on localized regions of the renal artery and adjacent regions of the renal plexus (RP), which lay within or adjacent to the adventitia of the renal artery. The application of thermal heating can achieve neuromodulation along all or a portion of the RP.

Desired effects of thermal heating may include raising the temperature of target neural fibers above a desired threshold to achieve non-ablative or ablative thermal alteration (e.g., via sustained heating and/or resistive heating). For example, the threshold temperature can be above body temperature (about 37° C.) but less than about 45° C. for non-ablative thermal alteration, or the threshold temperature can be about 45° C. or higher for ablative thermal alteration.

More specifically, exposure to thermal heating between about 37° C. and 45° C. may induce thermal alteration of the target neural fibers or of vascular structures that perfuse the target fibers. In cases where vascular structures are affected, the target neural fibers are denied perfusion, resulting in necrosis of the neural tissue. Exposure to thermal heating above 45° C. (or above 60° C. in other cases) may induce thermal ablation of the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the level or type of heat exposure utilized to induce thermal neuromodulation, a reduction in renal sympathetic nerve activity ("RSNA") is expected.

II. Selected Embodiments of Catheter Apparatus

FIG. 1 illustrates a system 1 in accordance with an embodiment of the present technology. The system 1 includes a renal neuromodulation system 10 ("system 10"). The system 10 includes an intravascular or intraluminal treatment device 12 that is operably coupled to an energy source or console 26. Energy source or console 26 can include, for example, an RF energy generator, a cryotherapy console, an ultrasonic signal generator or other energy source. In the embodiment shown in FIG. 1, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a therapeutic assembly or treatment section 21 at the distal portion 20 of the shaft 16. The therapeutic assembly 21 can include an electrode (not shown), which may be configured to be delivered to a renal blood vessel (e.g., a renal artery) in a delivery state.

Upon delivery to the target treatment site within the renal blood vessel, the therapeutic assembly 21 is further configured to deliver energy at the treatment site and provide electrically induced and/or thermally induced renal neuromodulation in a deployment state. In various embodiments, the therapeutic assembly 21 may be configured to transform between the delivery and deployed states using various mechanisms. For example, in some embodiments, the therapeutic assembly 21 may be placed or transformed into the deployed state or arrangement via actuation, e.g., via an actuator 36, such as a knob, button, pin, or lever carried by the handle 34.

The proximal end of the therapeutic assembly 21 is carried by or affixed to the distal portion 20 of the elongated shaft 16. A distal end of the therapeutic assembly 21 may terminate with, for example, an atraumatic rounded tip or cap. Alternatively, the distal end of the therapeutic assembly 21 may be configured to engage another element of the system 10 or treatment device 12. For example, the distal end of the therapeutic assembly 21 may define a passageway for engaging a guide wire (not shown) for delivery of the treatment device using over-the-wire ("OTW") or rapid exchange ("RX") techniques.

The energy source or console 26 is configured to generate a selected form and magnitude of energy for delivery to the target treatment site via therapeutic assembly 21. The energy generator 26 can be electrically coupled to the treatment device 12 via a cable 28. At least one supply wire (not shown) passes along the elongated shaft 16 or through a lumen in the elongated shaft 16 to the therapeutic assembly 21 comprising an electrode and transmits the treatment energy to the electrode. In some embodiments, the therapeutic assembly 21 may comprise multiple electrodes and each electrode includes its own supply wire. In other embodiments, however, two or more electrodes may be electrically coupled to the same supply wire. A control mechanism, such as foot pedal 32 or other operator control, may be connected (e.g., pneumatically connected or electrically connected) to the console to allow the operator to initiate, terminate and/or adjust various operational characteristics of the energy generator such as power delivery.

The system 10 may also include a remote control device (not shown) that can be positioned in a sterile field and operably coupled to the therapeutic assembly 21. The remote control device can be configured to allow for selective activation of the therapeutic assembly 21. For example, the remote control device can be configured to allow the operator to initiate, terminate and, optionally, adjust various operational characteristics of the energy generator. In some embodiments, a control mechanism (not shown) may be built into the handle assembly 34, allowing the operator control through the actuation of buttons, switches or other mechanisms on the handle assembly 34.

The energy source 26 can be configured to deliver the treatment energy under the control of a control algorithm 30, under the control of the clinician, or a combination thereof. In various embodiments, the control algorithm 30 may control current delivered to the electrode(s) comprised in the therapeutic assembly 21. In addition, the energy source or console 26 may include one or more evaluation or feedback algorithms 31 that can be configured to accept information and provide feedback to the clinician before, during, and/or after therapy. Feedback can be audible, visual or haptic. The feedback can be based on output from a monitoring system (not shown). The monitoring system can be a system including sensors or other monitoring devices integrated with treatment device 12, sensors or other monitoring devices separate from treatment device 12, or a combination thereof. The monitoring devices of the monitoring system can be configured to measure conditions at the treatment site (e.g., the temperature of the tissue being treated), systemic conditions (e.g., patient vital signs), or other conditions germane to the treatment, health, and safety of the patient.

Figure 2:
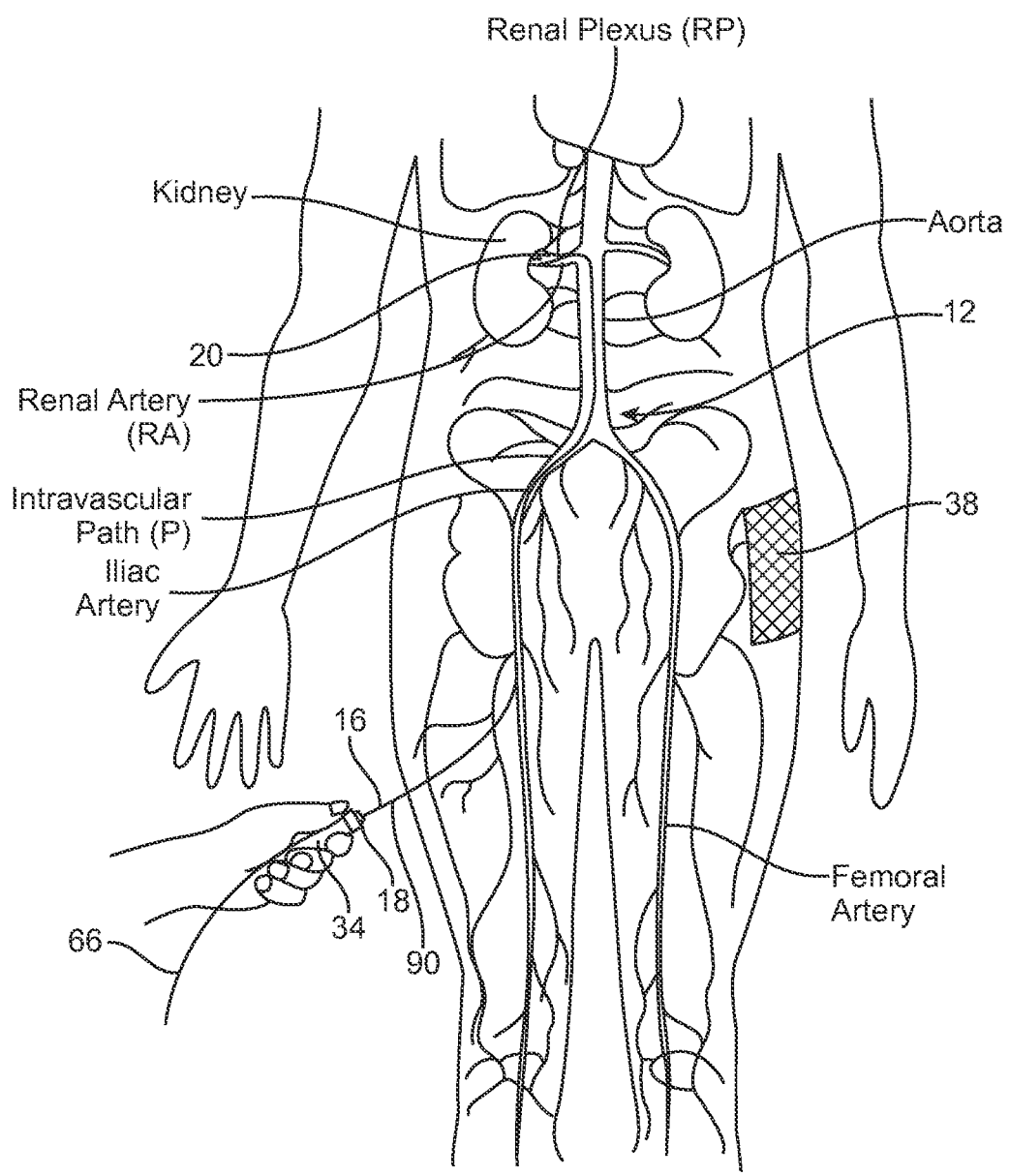
FIG. 2 illustrates one example of modulating renal nerves with an embodiment of the system illustrated in FIG. 1.

In some embodiments, the system 10 may be configured to provide delivery of a monopolar electric field via the therapeutic assembly 21. In such embodiments, a neutral or dispersive electrode 38 may be electrically connected to the energy generator 26 and attached to the exterior of the patient (as shown in FIG. 2). Additionally, one or more sensors (not shown), such as one or more temperature (e.g., thermocouple, thermistor, etc.), current, voltage, power, impedance, pressure, optical, flow, chemical or other sensors, may be located proximate to or within the electrode comprised in the therapeutic assembly and connected to one or more supply wires (not shown). For example, a total of two supply wires may be included, in which both wires could transmit the signal from the sensor and one wire could serve dual purpose and also convey the energy to the therapeutic assembly 21. Alternatively, a different number of supply wires may be used to transmit energy to the therapeutic assembly 21.

The energy source 26 can further include a device or monitor that may include processing circuitry such as one or more microprocessors, and a display 33. The processing circuitry may be configured to execute stored instructions relating to the control algorithm 30. The energy source 26 may be configured to communicate with the treatment device 12 (e.g., via the cable 28) to control the neuromodulation assembly and/or to send signals to or receive signals from the monitoring system. The display 33 may be configured to indicate power levels or sensor data visually, by audio, or other means, or may be configured to communicate the information to another device. The console 26 may also be operably coupled to a catheter lab screen or system for displaying treatment information (e.g., nerve activity before and after treatment, effects of ablation, efficacy of ablation of nerve tissue, lesion location, lesion size, etc.).

The energy source or console 26 can be configured to control, monitor, supply, or otherwise support operation of the treatment device 12. In other embodiments, the treatment device 12 can be self-contained and/or otherwise configured for operation without connection to the energy source or console 26. As shown in the example of FIG. 1, the energy source or console 26 can include a primary housing having a display 33.

In some embodiments, the energy source or console 26 can include a processing device or module (not shown) having processing circuitry such as a microprocessor. The processing device can be configured to execute stored instructions relating to the control algorithm 30, the evaluation/feedback algorithm 31 and other functions. Furthermore, the energy source or console 26 can be configured to communicate with the treatment device 12 via cable 28. For example, the therapeutic assembly 21 of the treatment device 12 can include a sensor (not shown) (e.g., a recording electrode, a temperature sensor, a pressure sensor, or a flow rate sensor) and a sensor lead (not shown) (e.g., an electrical lead or a pressure lead) configured to carry a signal from the sensor to the handle 34. The cable 28 can be configured to carry the signal from the handle 34 to the energy source or console 26.

The energy source or console 26 can have different configurations depending on the treatment modality of the treatment device 12. For example, when the treatment device 12 is configured for electrode-based or transducer-based treatment, the energy source or console 26 can include an energy generator (not shown) configured to generate RF energy, pulsed energy, microwave energy, optical energy, focused ultrasound energy, heat energy, or another suitable type of energy. In some embodiments, the energy source or console 26 can include an RF generator operably coupled to one or more electrodes (not shown) of the therapeutic assembly 21.

FIG. 2 illustrates one example of modulating renal nerves with an embodiment of the system 10. In this embodiment, the treatment device 12 provides access to the renal plexus (RP) through an intravascular path (P), such as a percutaneous access site in the femoral (illustrated), brachial, radial, or axillary artery to a targeted treatment site within a respective renal artery (RA). As illustrated, a section of the proximal portion 18 of the shaft 16 is exposed outside the patient. By manipulating the proximal portion 18 of the shaft 16 from outside the intravascular path (P), the clinician may advance the shaft 16 through the intravascular path (P) and remotely manipulate the distal portion 20 of the shaft 16. Image guidance technology, for example, computed tomography (CT), fluoroscopy, intravascular ultrasound (IVUS), optical coherence tomography (OCT), or another suitable guidance modality, or combinations thereof, may be used to aid the clinician's manipulation. Furthermore, in some embodiments image guidance components (e.g., IVUS, OCT) may be incorporated into the treatment device 12.

After the therapeutic assembly 21 is adequately positioned in the renal artery (RA), it can be radially expanded or otherwise deployed using the handle 34 or other suitable means until the neuromodulation assembly is positioned at its target site and the nerve-monitoring device is in stable contact with the inner wall of the renal artery (RA). Energy is then applied from the neuromodulation assembly to induce one or more desired neuromodulating effects on localized regions of the renal artery and adjacent regions of the renal plexus (RP), which lay intimately within, adjacent to, or in close proximity to the adventitia of the renal artery (RA). The application of energy may achieve neuromodulation along all or at least a portion of the renal plexus (RP).

In some embodiments, the therapeutic assembly 21 may function with multiple electrodes. When multiple electrodes are provided, the electrodes may deliver power independently (i.e., may be used in a monopolar fashion), either simultaneously, selectively, or sequentially, and/or may deliver power between any desired combination of the elements (i.e., may be used in a bipolar fashion). Furthermore, a user may choose which electrode(s) are used for power delivery in order to form highly customized lesion(s) within the renal artery having a variety of shapes or patterns.

Examples of therapeutic assemblies 21 that are suitable for use with the disclosed technology are described in more detail in U.S. Patent Application Publication No. 2011-0060324, filed Oct. 22, 2010, and titled Apparatus, Systems, and Methods for Achieving Intravascular, Thermally-Induced Renal Neuromodulation; and U.S. Patent Publication No. 2012-0116383, filed Oct. 25, 2011 and titled Catheter Apparatus Having Multi-Electrode Arrays for Renal Neuromodulation and Associated Systems and Methods; each of which are incorporated by reference herein in their entireties.

Figure 3A:
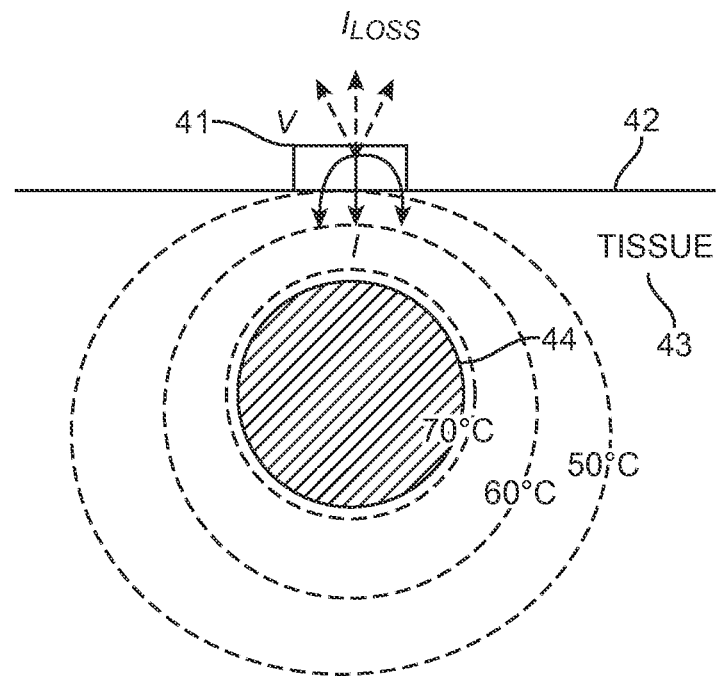
FIG. 3A illustrates an example of an electrode and the temperature zones created in adjacent tissue as a result of energy delivered to the electrode.

FIG. 3A illustrates an example RF electrode and the temperature zones created in adjacent tissue. Particularly, FIG. 3A illustrates temperatures zones created as a result of RF energy delivered into tissue 43 by electrode 41. Consider an example in which RF energy is provided to the electrode 41 such as, for example, by energy generator 26. In this example, electrode 41 emits RF energy to create a lesion. Particularly, the RF energy emitted by electrode 41 causes the tissue temperature to increase. This increase in tissue temperature can occur in isothermal regions as the example of FIG. 3A illustrates. In the illustrated example, three isotherms (shown by dashed lines) are illustrated; one at 50° C., one at 60° C. and one at 70° C. Also in the illustrated example, the region at the desired treatment temperature is illustrated by desired temperature region 44.

The voltage V at the electrode 41 causes a current I to flow through the electrode 41, through the surface of the vessel wall 42 and into the tissue 43. When the therapeutic assembly 21 is in the deployed state, one or more portions of the electrode 41 may be in stable contact with the vessel wall 42 to create desired lesions. The current density in the tissue excites the tissue, causing it to heat, forming the desired lesion. Cooling effects, due, for example, to the flow of blood or saline in the area where electrode 41 contacts vessel wall 42 can result in lower temperatures near the vessel wall 42. In order to reliably create consistent lesions, it is important to control the current density in the tissue.

In some patients, it may be desirable to create a single lesion or multiple focal lesions that are spaced around the circumference of the renal artery. One of ordinary skill in the art would understand that one or more electrodes 41 may be deployed to create a single lesion with desired longitudinal and/or circumferential dimensions, one or more full-circle lesions, multiple circumferentially spaced focal lesions at a common longitudinal position, spiral-shaped lesions, interrupted spiral lesions, generally linear lesions, and/or multiple longitudinally spaced discrete focal lesions at a common circumferential position. In still further embodiments, lesions having a variety of other geometric shapes or patterns may be created.

In various embodiments, one or more electrodes 41 may be operated in a monopolar or unipolar mode. In this arrangement, a return path for the applied RF electric field is established, e.g., by an external dispersive electrode (shown as element 38 in FIGS. 1 and 2), also called an indifferent electrode or neutral electrode. The monopolar application of energy (e.g., RF electric field energy) serves to ohmically or resistively heat tissue in the vicinity of the electrode 41. The application of the energy thermally injures tissue with the goal of inducing necrosis, thermal alteration or ablation in the targeted neural fibers. This thermal injury forms the desired lesion.

Conventional techniques that rely on power control can have difficulty creating consistent lesions in patients. The power delivered is a function of current and impedance. At a given power level, as tissue impedance increases, the delivered current, and hence, applied current density decreases. Because the impedance of the tissue can vary from patient to patient, control algorithms that rely on power control can have difficulty creating lesions at a desired level of consistency. To avoid the issues created by this anatomical variability and create more consistent lesions systems and methods can be implemented to control the energy delivered to the electrode using current control algorithms, rather than power control algorithms.

The active surface area of the electrode 41 is defined as the energy transmitting area that may be placed in intimate contact against tissue. A larger than intended contact area between the electrode and the vessel wall may cause excessively high temperatures at or around the interface between the tissue and the electrode, thereby generating excessive heat. Excessive heat may injure non-targeted tissue. Too little contact between the electrode and the vessel wall may result in superficial heating of the vessel wall, thereby resulting in an insufficient lesion (e.g., <10% of vessel circumference) and/or a lesion that is too shallow.

Figure 3B:
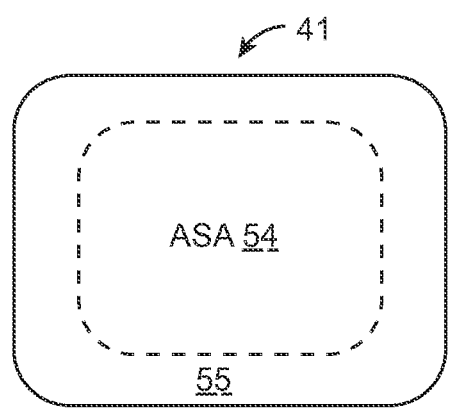
FIG. 3B illustrates an example of a surface of an electrode having an active surface area and a passive surface area.

Ablation is a function of current density from the electrode into the tissue. Controlling the active surface area of the electrode can also facilitate controlling current density. FIG. 3B is a diagram illustrating an example of an electrode having an active surface area as a subset of the total surface area in accordance with one embodiment of the technology described herein. As shown in FIG. 3B, the surface area of an electrode 41 includes a defined active surface area (ASA) 54 and an inactive, or passive surface area 55. In the example shown, the active surface area 54 and the passive surface area 55 make up the total surface area (TSA) of the contact face of electrode 41.

The active surface area of contact (ASA) between the electrode 41 and the inner vessel wall (e.g., renal artery wall 42) affects the efficiency and control of the generation of a thermal energy field across the vessel wall to thermally affect targeted neural fibers in the renal plexus. The ASA also affects the current density delivered to the tissue.

The higher the current density for a given electrode the greater the tissue excitation, which translates into more heat being generated within the tissue. For example, given an electrode of size $ASA_1$ and a current $I_1$ through the electrode, the system will supply a current field gradient into the tissue G1, where the high current density areas define the ablation zone of the tissue. If the electrode area increases but the current through it is maintained as $I_1$ there will be more dispersion of the current field gradient into the tissue. While there is more area in the tissue that is impacted (based on the larger ASA), the intensity of the current field through this area decreases, which results in a decreased current density.

Without control of the area of contact of the electrode with the tissue, the current density into the tissue can vary dramatically, there can be a small contact point with a strong field (high current density), or a large area of contact with a weak field (low current density), all of which can produce inconsistent ablations. Therefore, controlling the area of contact and the current through that area, controls the ablation achieved regardless of patient, blood flow, etc. thereby providing a consistent ablation each time.

While the ASA of the electrode is an important parameter for creating lesions, the ratio between the ASA and total surface area (TSA) of the electrode 41 is also important. The ASA to TSA ratio influences lesion formation due to the effects of blood flow or other convective cooling elements such as injected or infused saline. For example, blood or saline flowing over the entire electrode, including the inactive portion of the electrode, provides conductive and convective cooling of the electrode, carrying excess thermal energy away from the interface between the vessel wall and electrode.

As noted above, the energy delivered by electrode 41 may create different temperature zones in the tissue. It is desirable to control the energy delivered to the electrode 41 and the amount of cooling provided by blood or saline, such that the desired temperature zone 44 covers or overlaps the region where most of the nerves exist. Because most of the nerves are generally 2-3 mm away from the surface 42 of the artery, some embodiments place desired temperature zone 44 approximately 2-3 mm from the surface 42 of the artery. As shown in FIG. 3A, this can be accomplished without increasing the temperature of the tissue 43 between the electrode 41 and zone 44 above the target temperature for zone 44. Indeed, as FIG. 3A illustrates, the tissue 43 between the electrode 41 and zone 44 can be maintained at a temperature below the target temperature (below 70° C. in this example). To control placement and temperature of the desired temperature zone 44 without charring tissue at the vessel wall or damaging tissue adjacent the treatment site, embodiments can be implemented to control the energy delivered to the electrode 41 and the amount of cooling provided by convention or conduction.

In various embodiments, the electrode 41 is configured to maintain a constant ASA by maintaining a consistent, known contact area with the surface 42 of the artery. For example, electrode 41 can be configured such that the surface area of the electrode 41 comprises an active area and a passive area as shown in FIG. 3B. In some configurations, the active area may be provided in a central region of the electrode, and the passive area provided along the edges of the electrode contact surface thereby surrounding the active region. The areas of the active and passive regions may be defined to allow the active area to maintain a more consistent contact with the vessel wall in circumstances where less than perfect physical placement is attained—e.g., even when the electrode is positioned with an angle of inclination >0° relative to the vessel wall. Providing the active region in the center of the electrode accommodates, or is more tolerant to, non-zero angles of inclination by allowing an edge of the electrode to be 'lifted' away from the vessel wall, while still allowing the active center region to maintain full contact. This allows the effective contact area of the electrode to be maintained at a constant. Because current density is a function of surface area, maintaining a constant surface area allows current density to be controlled by controlling the current. When energy is delivered to the electrode 41, the current density delivered to the tissue determines the temperature zones and their placement. Accordingly, current control algorithms can also be used to control placement of the temperature zones including the desired temperature zone.

III. Applying and Controlling Energy Delivered to Tissue Via the Electrode

1. Overview

Referring again to FIG. 1, the energy generator 26 may supply a continuous or pulsed RF electric field to the electrode(s). Although a continuous delivery of RF energy is an option, the application of RF energy in pulses may allow the application of relatively higher energy levels (e.g., higher power), at a duty cycle chosen to attain the desired lesion while providing less discomfort than continuous RF. Pulsed energy may also allow for the use of a smaller electrode.

During treatment, various treatment parameters may be monitored via data collected with one or more sensors. The monitored parameters can provide feedback regarding the treatment. Sensors can include, for example, temperature sensors (e.g., thermocouples, thermistors, etc.), voltage sensors, current sensors, impedance sensors, pressure sensors, optical sensors, flow sensors, chemical sensors, etc., which may be incorporated into or on the therapeutic assembly 21, the electrode, and/or in/on adjacent areas on the distal portion 20. A sensor may be incorporated into the therapeutic assembly 21 in a manner that specifies whether the sensor(s) are in contact with tissue at the treatment site and/or are facing blood flow. The ability to specify sensor placement relative to tissue and blood flow is highly significant, since a temperature gradient across the electrode from the side facing blood flow to the side in contact with the vessel wall may be up to about 15° C. Significant gradients across the electrode in other sensed data (e.g., flow, pressure, impedance, etc.) also are expected.

The sensor(s) may, for example, be incorporated on the side of the electrode that contacts the vessel wall at the treatment site during power and energy delivery or may be incorporated on the opposing side of the electrode that faces blood flow during energy delivery, and/or may be incorporated within certain regions of the electrode (e.g., distal, proximal, quadrants, etc.). In some embodiments, multiple sensors may be provided at multiple positions along the electrode or therapeutic assembly 21 and/or relative to blood flow. For example, a plurality of circumferentially and/or longitudinally spaced sensors may be provided. In one embodiment, a first sensor may contact the vessel wall during treatment, and a second sensor may face blood flow.

Additionally or alternatively, various microsensors may be used to acquire data corresponding to the electrode, the vessel wall and/or the blood flowing across the electrode. For example, arrays of micro thermocouples and/or impedance sensors may be implemented to acquire data along the electrode or other parts of the treatment device. Sensor data may be acquired or monitored prior to, simultaneous with, or after the delivery of energy or in between pulses of energy, when applicable. The monitored data may be used in a feedback loop to better control therapy, e.g., to determine whether to continue or stop treatment, and it may facilitate controlled delivery of an increased or reduced power or a longer or shorter duration therapy.

A treatment administered using the system 10 constitutes delivering energy through the electrodes to the inner wall of a renal artery for a predetermined amount of time (e.g., 120 sec). Multiple treatments (e.g., 4-6) may be administered in both the left and right renal arteries to achieve the desired coverage. A technical objective of a treatment may be, for example, to heat tissue to a desired depth (e.g., at least about 3 mm) or at a desired region to a temperature that would lesion a nerve (e.g., about 65° C.) A typical clinical objective of the procedure is to neuromodulate (e.g., lesion) a sufficient number of renal nerves (either efferent or afferent nerves of the sympathetic renal plexus) to cause a reduction in sympathetic tone. If the technical objective of a treatment is met (e.g., tissue is heated to about 65° C. at a depth of about 3 mm), the probability of forming a lesion of renal nerve tissue is high. The greater the number of technically successful treatments, the greater the probability of modulating a sufficient proportion of renal nerves, and thus the greater the probability of clinical success.

Throughout the treatment there may be a number of states that are indicative of a possibility that the treatment may not be successful. In certain embodiments, based on indications of these states, the operation of the system 10 may be stopped or modified. For example, certain indications may result in cessation of energy delivery and an appropriate message may be displayed, such as on display 33. Factors that may result in a display message and/or cessation or modification of a treatment protocol include, but are not limited to, indications of an impedance, blood flow, and/or temperature measurement or change that is outside of accepted or expected thresholds and/or ranges that may be predetermined or calculated. A message can indicate information such as a type of patient condition (e.g., an abnormal patient condition), the type and/or value of the parameter that falls outside an accepted or expected threshold, an indication of suggested action for a clinician, or an indication that energy delivery has been stopped. However, if no unexpected or aberrant measurements are observed, energy may continue to be delivered at the target site in accordance with a programmed profile for a specified duration resulting in a complete treatment. Following a completed treatment, energy delivery is stopped and a message indicating completion of the treatment may be displayed.

However, a treatment can be completed without initiating an indication of an abnormal patient condition and yet an event or combination of events could occur that alters (e.g., decreases) the probability of a technically successful treatment. For example, an electrode that is delivering energy could move or be inadvertently placed with insufficient contact between the electrode and the wall of a renal artery, thereby resulting in insufficient lesion depth or temperature. Therefore, even when a treatment is completed without an indication of abnormal patient condition, it may be difficult to evaluate the technical success of the treatment. Likewise, to the extent that indications of abnormal patient conditions may be reported by the system 10, it may be difficult to understand the causes of the abnormal patient conditions (such as temperature and/or impedance values that fall outside of expected ranges).

As noted above, one or more evaluation/feedback algorithms 31 may be provided that are executed on a processor-based component of the system 10, such as one or more components provided with the generator 26. In such implementations, the one or more evaluation/feedback algorithms 31 may be able to provide a user with meaningful feedback that can be used in evaluating a given treatment and/or that can be used in learning the significance of certain types of abnormal patient conditions and how to reduce the occurrence of such conditions. For example, if a particular parameter (e.g., an impedance or temperature value) causes or indicates that treatment did not proceed as expected and (in some instances), may have resulted in a technically unsuccessful treatment, the system 10 can provide feedback (e.g., via the display 33) to alert the clinician. The alert to the clinician can range from a simple notification of unsuccessful treatment to a recommendation that a particular parameter of the treatment (e.g., the impedance value(s) during treatment, placement of the energy delivery elements 24 within the patient, etc.) be modified in a subsequent treatment. The system 10 can accordingly learn from completed treatment cycles and modify subsequent treatment parameters based on such learning to improve efficacy. Non-exhaustive examples of measurements the one or more evaluation/feedback algorithms 31 may consider include measurements related to change(s) in temperature over a specified time, a maximum temperature, a maximum average temperature, a minimum temperature, a temperature at a predetermined or calculated time relative to a predetermined or calculated temperature, an average temperature over a specified time, a maximum blood flow, a minimum blood flow, a blood flow at a predetermined or calculated time relative to a predetermined or calculated blood flow, an average blood flow over time, a maximum impedance, a minimum impedance, an impedance at a predetermined or calculated time relative to a predetermined or calculated impedance, a change in impedance over a specified time, or a change in impedance relative to a change in temperature over a specified time. Measurements may be taken at one or more predetermined times, ranges of times, calculated times, and/or times when or relative to when a measured event occurs. It will be appreciated that the foregoing list merely provides a number of examples of different measurements, and other suitable measurements may be used.

2. Control of Applied Energy

Figure 4:
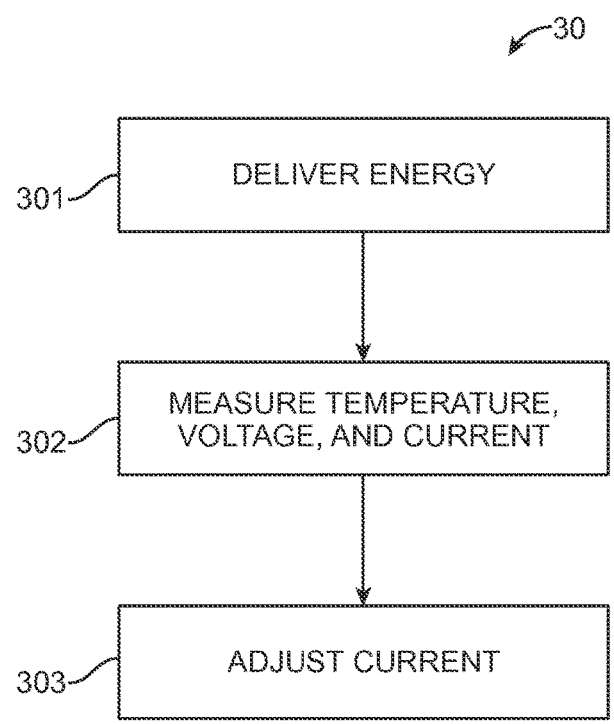
FIG. 4 illustrates a current control method 30 in accordance with one embodiment of the technology disclosed herein.

With the treatments disclosed herein for delivering therapy to target tissue, energy can be delivered to the target neural structures in a controlled manner. Various embodiments comprising a control algorithm that provides consistent current or current density regulation to control the amount of energy delivered in different cases, even though the tissue impedance Z may vary from patient to patient, vessel to vessel, or location to location within the vessel. The controlled delivery of energy can allow the thermal treatment to be controlled. Control of the current in conjunction with cooling effects of the blood or saline can be used to cause the thermal zone to extend into the renal fascia while reducing undesirable energy delivery or thermal effects to the vessel wall. A controlled delivery of energy may also result in a more consistent, predictable and efficient overall treatment. Accordingly, the generator 26 desirably includes a processor including a memory component with instructions for executing an algorithm 30 (see FIG. 1) for controlling the delivery of power and energy to the energy delivery device through the control of delivered current. The algorithm 30, a representative embodiment of which is depicted in FIG. 4, may be implemented as a conventional computer program for execution by a processor coupled to the generator 26. A clinician using step-by-step instructions may also implement the algorithm 30 manually.

FIG. 4 illustrates a current control method 30 in accordance with one embodiment of the technology disclosed herein. At step 301, the energy generator may be controlled to deliver energy (e.g., RF energy) to an electrode included with therapeutic assembly 21. In various embodiments, such control may be provided by the current control method or the current control algorithm 30. At step 302, feedback regarding one or more treatment metrics may be measured or received. For example, in some embodiments, a temperature, a voltage, and a current of the electrode may be measured. The temperature, the voltage, and the current measured may be used as feedback to determine whether the amount of energy delivered to the electrode should be maintained, increased or decreased. At step 303, the current delivered to the electrode may be adjusted according to the feedback obtained.

In some embodiments, the current delivered can be measured or calculated. Given a known current, the current density can be calculated based on the active surface area (ASA) of the electrode. Impedance can also be measured or calculated using measured voltage and current.

In some embodiments, the ASA of an electrode may be measured, known or otherwise determined, and the current density delivered by the electrode may be adjusted by adjusting current delivered to the electrode given the known ASA. Furthermore, in one embodiment, an optimal current density for a vessel may be determined via factors provided by various sensors such as, for example, the voltage, the current, the temperature, the power, the blood temperature, the blood flow, etc. The optimal current density for different vessels may vary and energy levels may be adjusted so that the current density delivered to the tissue is an optimal current density.

In various embodiments, the current (or current density) delivered may be adjusted by increasing or decreasing the current (or current density) in a linear or non-linear fashion over time, as a function of a change in temperature, as a function of impedance, or as a function of power.

In some embodiments, a limit to which the current (or current density) can be adjusted may be reached. That is, the instantaneous rate of change of the current (or current density) may be limited to the maximum change in current (or current density). In various embodiments, the current control method or the current control algorithm 30 may determine the maximum change in current (or current density) by using a maximum current level of the electrode, a maximum temperature of the vessel, a maximum power of the electrode, and a maximum change in impedance of the vessel. In further embodiments, the current control method or the current control algorithm 30 may override the limit by using the feedback provided by the sensors such as the temperature, the power, the impedance to adjust (i.e., increase or decrease) the current or current density delivered to the electrode.

During the treatment, the impedance of the tissue may change due to the change of the tissue structure as a result of neuromodulation. The current control method or the current control algorithm 30 may measure the impedance of the tissue or the change of impedance to determine whether the current delivered to the electrode or the current density of the tissue should be adjusted (i.e., increased or decreased). This can help to reduce the risk that a maximum current ($I_{MAX}$), maximum tissue temperature or other limit is not exceeded.

In further embodiments, timing of termination or suspension of a treatment may be determined. Accordingly, delivery of energy to the electrode may be terminated, thereby terminating delivery of current to the tissue based on one or more predetermined thresholds being reached. These thresholds can include, for example, a predetermined maximum amount of time for which energy can be delivered, a predetermined target temperature value, a predetermined target current value, a predetermined cumulative amount of current delivered (e.g., current integrated over time), or a predetermined change (increase or decrease) in impedance of the tissue.

Figure 5:
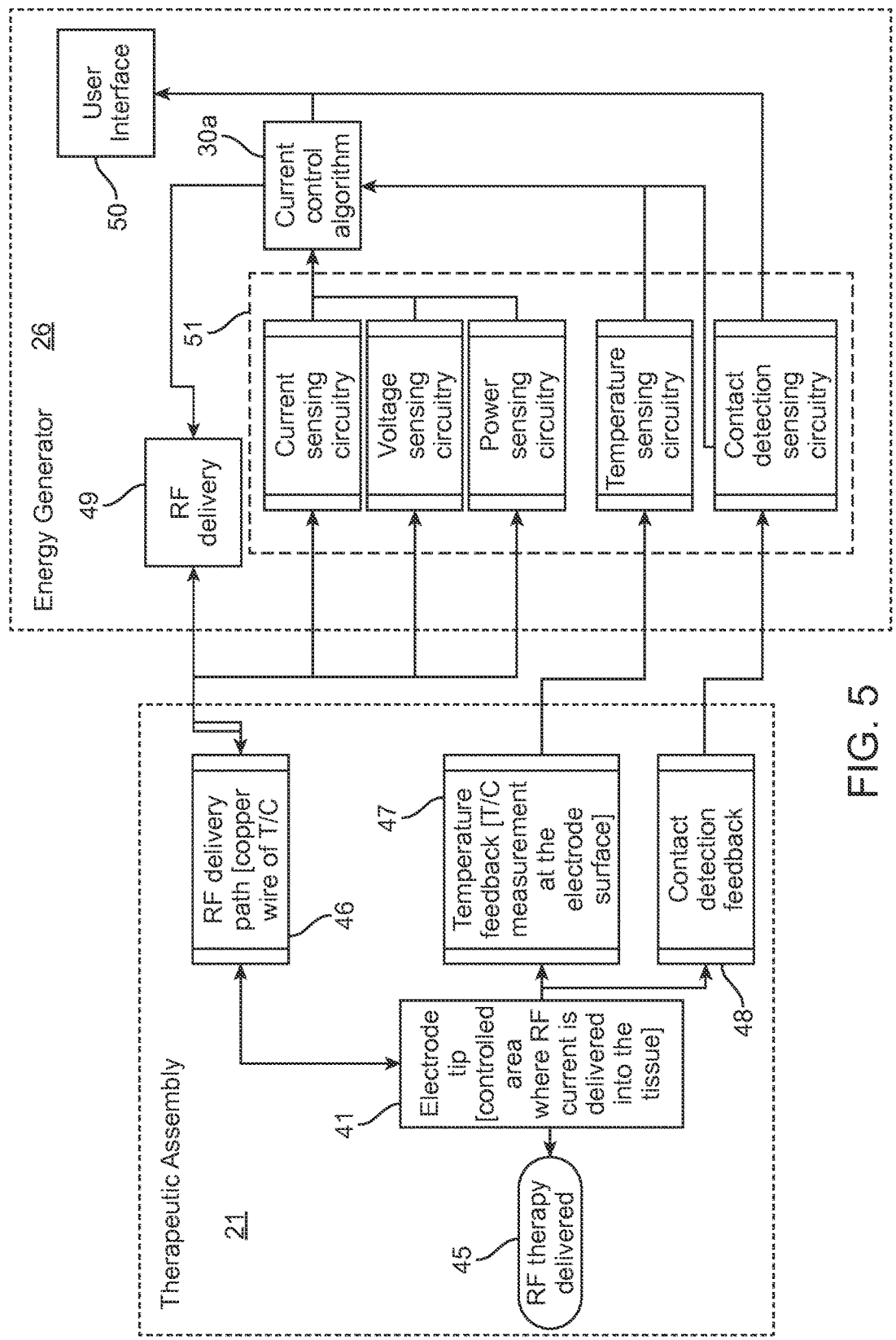
FIG. 5 illustrates a control block diagram implementing a control method or the control algorithm in accordance with one embodiment of the technology disclosed herein.

FIG. 5 illustrates a control block diagram implementing the control method or the control algorithm 30 in accordance with one embodiment of the technology disclosed herein. The illustrated example shows a therapeutic assembly 21 including an electrode 41 to deliver RF therapy 45 to the target tissue. The example also shows the RF delivery path 46 by which RF energy is delivered to the electrode from energy generator 26.

One or more feedback loops are provided by measuring various operating parameters. The operating parameters monitored in accordance with the algorithm may include, for example, temperature, time, current, voltage, impedance, power, contact area, blood flow, flow velocity, volumetric flow rate, blood pressure, heart rate, etc. The illustrated example shows sensor(s) 47, to measure temperature at the electrodes(s), and a mechanism to detect contact 48 and hence contact area of the one or more electrodes 41 during treatment.

Temperature can be measured at the electrode surface for example, and a maximum electrode temperature set. Discrete values in temperature may be used to trigger changes in power or energy delivery. For example, high values in temperature could indicate tissue desiccation. Accordingly, when a predetermined maximum temperature (e.g., 85° C.) is reached, the algorithm may decrease or stop the power and energy delivery to prevent undesirable thermal effects to target or non-target tissue. Time additionally or alternatively may be used to prevent undesirable thermal alteration to target or non-target tissue. For each treatment, a set time (e.g., 2 minutes) is defined to prevent indefinite delivery of power. Accordingly, although not illustrated, a timer can be included (e.g., as part of control algorithm 30) to determine the amount of time energy is applied.

Energy generator/console 26 in this example includes current control algorithm 30a, which in some embodiments can be a subset of an overall algorithm or set of control algorithms 30. Current control algorithm 30a, as is the case with control algorithm 30, can be run on a processor or other computing module (not shown). RF delivery module 49 can include an RF signal generator to generate the RF energy used for treatment. An RF signal generator can include an oscillator (e.g., a frequency synthesizer) to generate a time varying signal and an amplifier to amplify the oscillator output to desired signal levels. An attenuator, such as a variable attenuator, can also be included to allow more accurate control of the output power levels. The oscillator, amplifier and attenuator can be controlled by the processor or computing module to control parameters such as the frequency and power level of the RF signal generated. Operator control can be provided, for example, by a user interface to provide manual control of the RF generator. Also, control algorithm 30 (including current control algorithm 30a) can control the output of the RF generator.

Also shown in FIG. 5 are a plurality of sensor modules 51 that can be used to sense parameters such as, for example, current, voltage, power, temperature and contact detection. Information from sensor modules 51 can be used by current control algorithm 30a to determine how to control the current of the therapy delivered.

Impedance of the tissue may be used to measure tissue changes. Impedance indicates the electrical property of the treatment site. In thermal inductive embodiments, when an electric field is applied to the treatment site, the impedance will decrease as the tissue cells are treated, and the cells will become less resistive to current flow. If too much energy is applied, tissue desiccation or coagulation may occur near the electrode, which would increase the impedance as the cells lose water retention and/or the electrode surface area effectively decreases (e.g., via the accumulation of coagulum). Thus, an increase in tissue impedance may be indicative or predictive of undesirable thermal alteration to target or non-target tissue. In other embodiments, the impedance value may be used to assess contact of the electrode with the tissue. For multiple electrode configurations (e.g., when the therapeutic assembly 21 comprises two or more electrodes,) a relatively small difference between the impedance values of the individual electrodes may indicate good contact with the tissue. For a single electrode configuration, a stable value may indicate good contact. Accordingly, impedance information from the one or more electrodes may be provided to a downstream monitor, which in turn may provide an indication to a clinician related to the quality of the electrode contact with the tissue.

Additionally or alternatively, power is an effective parameter to monitor in controlling the delivery of therapy. Power is a function of voltage and current. The algorithm 30 may tailor the voltage and/or current to achieve a desired power.

Derivatives of the aforementioned parameters (e.g., rates of change) also may be used to trigger changes in power or energy delivery. For example, the rate of change in temperature could be monitored such that power output is reduced in the event that a sudden rise in temperature is detected. Likewise, the rate of change of impedance could be monitored such that power output is reduced in the event that a sudden rise in impedance is detected.

Figure 6:
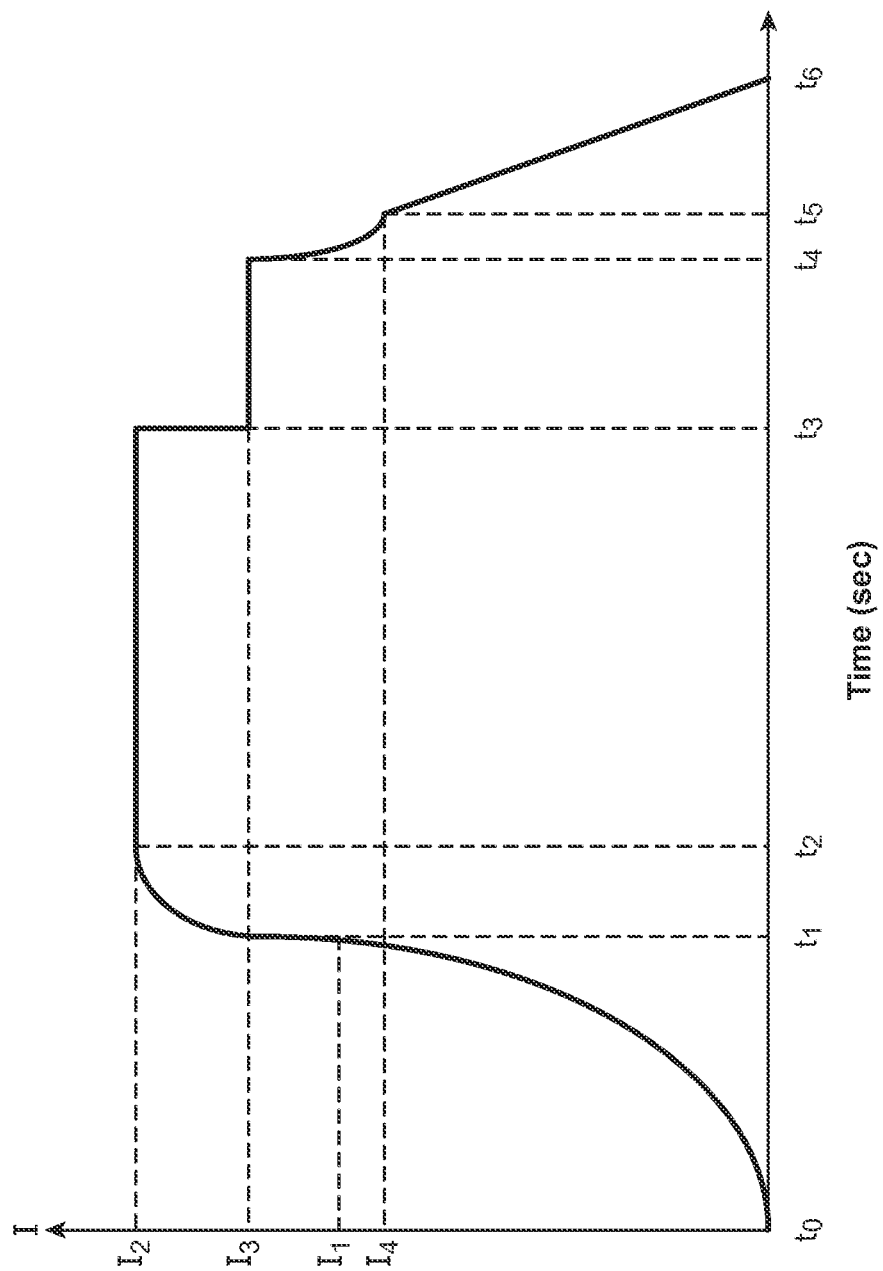
FIG. 6 is a graph illustrating a current control algorithm in accordance with one embodiment of the technology described herein.

FIG. 6 is a graph illustrating a current control algorithm in accordance with one embodiment of the technology described herein. FIG. 6 plots an example application of current being controlled as a function of treatment time. The amount of current delivered by energy generator 26 to an electrode can be controlled by controlling the voltage. In the illustrated example, the current is controlled such that it is ramped up to a targeted operating current $I_2$, which is just below a maximum operating current $I_{MAX}$. In some embodiments, $I_2$ may be the predetermined maximum current $I_{MAX}$, or it may be a value lower than $I_{MAX}$. In various embodiments, the current is controlled with the goal of delivering a particular current density based on a known active area of the electrode used in the treatment.

When a treatment is initiated (e.g., via the foot pedal 32 illustrated in FIG. 1), the control algorithm 30 instructs the generator 26 to gradually increase current delivered to the electrode to a first current threshold I1 over a first time period $t_0$-t1. The current increase during the first time period $t_0$-t1 may be linear with a constant rate of increase or nonlinear (e.g., exponential or parabolic or otherwise) with a variable rate of increase. In the illustrated example, the current is increased nonlinearly. A gradual increase is applied at startup, and the current increases more rapidly as it reaches I1. The average rate at which the energy generator 26 increases its current output during this period may be calculated as $I1/(t1-t_0)$. One reason a gradual increase from $t_0$-$t_1$ can be provided is to allow the system the opportunity to measure properties such as power, tissue temperature and the like while the current is being applied.

Once the current to the electrode reaches the value of I1, the algorithm may increase the current at a second rate to I2 over a predetermined period of time t1-t2. Accordingly, in the illustrated example, $I_1$ is a transition point changing the rate (or the equation used to apply the rate) of current increase. This transition current $I_1$ can be chosen, for example, as the minimum current threshold of a known operating efficiency. Also, it can be identified as the current at which the electrode is sufficiently energized such that ablation can begin to occur. Also, measurements of a tissue property being reached (such as, for example, temperature) indicate current should be reduced or leveled off.

Again, the rate of increase between time t1-t2 can be linear or non-linear and in the illustrated example, a nonlinear rate of increase is applied. As illustrated, as the current approaches the target delivery current $I_2$, the rate of increase is diminished, providing a gradual approach to the target $I_2$. As with the period from $t_0$-$t_1$, one reason a gradual increase from $t_0$-$t_1$ can be provided is to allow the system the opportunity to measure properties such as power, tissue temperature and the like while the current is being applied. This can help to reduce the risk that a maximum current ($I_{MAX}$), maximum tissue temperature or other limit is not exceeded. Also, because the impedance of the tissue is unknown for a given patient until calculated, and may change during the course of a treatment, a gradual increase in current can help to ensure that the maximum current levels will not be exceeded.

This current ramp in predetermined increments over predetermined periods of time may continue until the target treatment current (e.g., I2) is achieved or some other condition is satisfied. The algorithm may maintain the target current I2 for a desired period of time or up to the desired total treatment time.

The target treatment current $I_2$ can be maintained for a calculated or predetermined treatment time. In some embodiments, treatment time is determined as a function of time while in other embodiments other factors can determine treatment time. For example, the current delivered can be integrated as a function of ablation time and the treatment continued until a desired total amount of current is delivered.

The system can be configured to monitor parameters such as delivered current (e.g., based on current measured in the return path), electrode or tissue temperature, power levels and impedance, for example. Such measurements can be made throughout the treatment time or at determined times during treatment. The current in various embodiments can be controlled to ensure that the operating current does not cause predetermined maximum values for these parameters to be exceeded. Accordingly, if one or more of the measured parameters reaches or is reaching its predetermined maximum value, the current can be reduced or terminated.

As a result of the treatment, impedance of the tissue may drop. This may result in an increase in delivered current at a constant voltage. Accordingly, the algorithm can be configured to monitor the current and decrease the voltage to maintain the desired amount of current.

In the illustrated embodiment, the current is dropped from $I_2$ to $I_3$ at time $t_3$ and maintained at $I_3$ until time $t_4$. This can be done, for example, to avoid the tissue reaching an undesirably high temperature. The decrease can be a step function as illustrated, or it can be a linear or nonlinear gradual decrease over time. Time $t_3$ may be reached, for example, in response to a condition such as tissue over temperature, for example. In such cases, the current delivered can be quickly dropped to a safe level (e.g., $I_3$) and maintained until $t_4$. Accordingly, a step-down is shown in the example. In other embodiments, as maximum temperature is reached, a gradual ramp down in current can be applied.

Subsequently, the energy generator 26 begins decreasing the current delivered to the electrode. This is illustrated at time $t_4$. The decision to begin decreasing the current may be based on the amount of current delivered over time and/or one or more of the parameters discussed above such as temperature, delivered power, and tissue impedance. The algorithm may decrease the current in the time period t4-t5 until a predetermined current value $I_4$ is reached or some other condition is satisfied. The algorithm may decrease the current delivered to the electrode at a predetermined rate over the time period t4-t5 in a linear or nonlinear fashion. Once the current to the electrode reaches the current value $I_4$, the algorithm may decrease the current delivered to the electrode at a different rate over the time period t5-t6. As a result, the energy generator 26 decreases its current output at a rate that is generally constant and may be calculated as $I4/(t6-t5)$. Alternatively, the current decrease may be nonlinear (e.g., exponential or parabolic) with a variable rate of decrease. In one embodiment, $t_5$ is determined based on the integral of the current delivered during the procedure.

The algorithm 30 can be implemented to monitor certain operating parameters (e.g., temperature, time, impedance, power, flow velocity, volumetric flow rate, blood pressure, heart rate, etc.) during the treatment process. The operating parameters may be monitored continuously or periodically. The algorithm 30 can be configured to check the monitored parameters against predetermined parameter profiles to determine whether the parameters individually or in combination fall within or outside of the ranges set by the predetermined parameter profiles. If the monitored parameters fall within the ranges set by the predetermined parameter profiles, then treatment may continue at the commanded power output or according to the default delivery profile. If monitored parameters fall outside the ranges set by the predetermined parameter profiles, the algorithm 30 adjusts the commanded power output accordingly. For example, if a target temperature (e.g., 65° C.) is achieved, then current delivery is kept constant until the total treatment time (e.g., 120 seconds) has expired. For example, in terms of the embodiment shown in FIG. 6, achievement of target temperature occurs at $t_2$, and that current level $I_2$ is held constant until $t_3$.

If a first temperature threshold (e.g., 70° C.) is achieved or exceeded, then the current is reduced in predetermined increments until a target temperature is achieved. In the example shown in FIG. 6, current is reduced in one step at $t_3$. This could be done in multiple increments. If a second temperature threshold (e.g., 85° C.) is achieved or exceeded, thereby indicating an undesirable condition, then current delivery may be terminated. The system may be equipped with various audible, visual or haptic alarms to alert the operator of certain conditions.

The following is a non-exhaustive list of events under which algorithm 30 may adjust and/or terminate or discontinue the commanded current output:
(1) The measured temperature exceeds a maximum temperature threshold (e.g., from about 70 to about 85° C.).
(2) The average temperature derived from the measured temperature exceeds an average temperature threshold (e.g., about 65° C.).
(3) The rate of change of the measured temperature exceeds a rate of change threshold.
(4) The temperature rise over a period of time is below a minimum temperature change threshold while the generator 26 has non-zero output. Poor contact between the electrode and the arterial wall may cause such a condition.
(5) A measured impedance exceeds or falls outside an impedance threshold (e.g., <125 Ohms or >1000 Ohms).
(6) A measured impedance exceeds a relative threshold (e.g., impedance decreases from a starting or baseline value and then rises above this baseline value)
(7) A measured power exceeds a power threshold (e.g.,).
(8) A measured duration of power delivery exceeds a time threshold (e.g., >120 seconds).

C. Technical Evaluation of a Treatment

Figure 7:
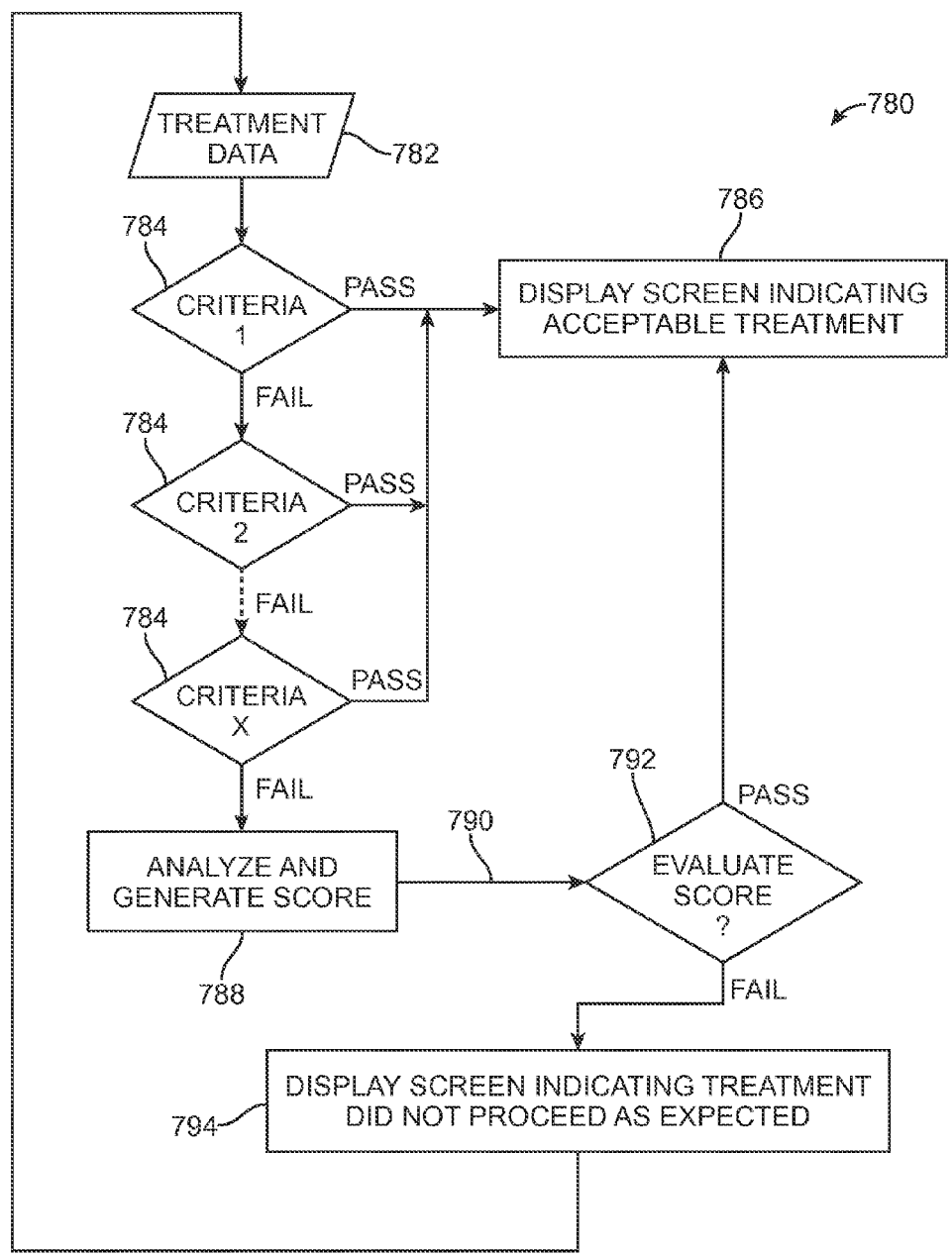
FIG. 7 is a block diagram illustrating a process for determining the efficacy of treatment in accordance with an embodiment of the present technology.

FIG. 7 is a block diagram illustrating a process for determining the efficacy of treatment in accordance with an embodiment of the present technology. Particularly, the process 780 is configured to evaluate events in a treatment, determine the probability of technical success of the treatment and display an appropriate message to provide feedback to an operator of the system 10 (or another suitable treatment system). If the treatment is determined to have a predetermined probability of sub optimal technical success, a message indicating that the treatment did not proceed as expected may be displayed. Alternative implementations can categorize a treatment into several ranges of probabilities of success, such as probability of success on a scale of 1 to 5. Similarly, in certain implementations, the process 780 can evaluate if a treatment belongs in a high probability of success category, a very low probability of success category, or somewhere in between.

Variables that characterize a treatment and that may be used by the algorithm 780 in evaluating potential efficacy of a treatment can include, but are not limited to: time (i.e., treatment duration), power, change in temperature, maximum temperature, mean temperature, blood flow, standard deviation of temperature or impedance, change in impedance, or combinations of these or other variables. For example, some or all of the variables may be evaluated at process 780 as treatment data 782. In this example of process 780, the treatment data 782 may be assessed by applying a plurality of criteria 784 to the treatment data 782 to determine whether the criteria are met. In the illustrated example, the criteria 784 are applied one at a time in a sequential fashion. Favorable assessment of the treatment data 782 in view of one of the criteria 784 may indicate a likelihood of successful treatment and result in feedback to the user indicating successful treatment at operation 786. In one example, the feedback is in the form of a message or visual alert being displayed on a display screen (e.g., display 33). Failure of the treatment data 782 to meet one of the criterion (or one set of criteria) 784 may result in the treatment data being evaluated in light of the next evaluation criterion 784.

In the depicted embodiment, failure of the treatment data to be found acceptable in view of all of the criteria 784 may result in an additional evaluation being performed. Particularly, the system can analyze the data 782 and generate a score as illustrated at operation 788. The output of the analysis and scoring operation (e.g., a score 790) may be evaluated (operation 792) to determine a likelihood of success or failure. Based on this evaluation 792, the treatment may be deemed acceptable, and the user alerted as to the success as illustrated by operation 786. On the other hand, where the treatment is deemed unacceptable or at a low likelihood of success, the user can be alerted as to this outcome at operation 794. The alert can include information (e.g., displayed on display screen 33) indicating the reason for the outcome. The operator can use this information to adjust the process, run tests or take other action as may be appropriate.

In still further embodiments, the operation 780 can include an automatic action in response to an indication that treatment did not proceed as expected. For example, the system can be configured to automatically change a treatment parameter (e.g., automatically adjust the current level) in response to the indication of a failure. The change in the treatment parameter can be made based on an indication of what criteria is listed as failing. For example, where the unmet criterion is the desired temperature, the system can be configured to automatically increase the current up to a defined maximum.

In other embodiments, the criteria may be evaluated in parallel rather than serially. Likewise, in other embodiments for the treatment to be determined to have passed the evaluation, all of the criteria must be passed.

D. Feedback Related to High Temperature Conditions

While the preceding describes generalized evaluation of the technical success of a treatment, another form of feedback that may be useful to an operator of the system 10 (FIG. 1) is feedback related to specific types of patient or treatment conditions. For example, the system 10 may generate a message related to high temperature conditions, over current conditions, high impedance conditions, or other parameter information. In particular, during a treatment while energy is being delivered, tissue temperature may increase above a specified level. A temperature sensor (e.g., thermocouple, thermistor, etc.) positioned at or near the electrode provides an indication of temperature in the electrode and, to some extent, an indication of tissue temperature. The electrode does not heat directly as energy is delivered to tissue. Instead, tissue is heated by the RF energy emitted by the electrode. Heat from the tissue conducts to the electrode and the temperature sensor in the electrode. Accordingly, an estimate of the tissue temperature and temperature zones can be made from the electrode temperature. In one implementation, the system 10 may cease energy delivery if the real time temperature rises above a predefined maximum temperature (e.g., 85° C.). In such an event, the system may generate a message indicating the high temperature condition. However, depending on the circumstances, different actions by the clinician may be appropriate. In further embodiments, the system can be configured to alert the clinician as one or more temperature points are reached, or if temperature is rising faster than a predetermined rate.

If tissue becomes too hot, established temperature thresholds can be exceeded. The implications of high tissue temperature are that an acute constriction of the artery or a protrusion of the artery wall could occur. This can happen right away or within a short time (e.g., about 50 seconds to about 100 seconds) after the occurrence of the high temperature is noted and a message is generated. In such an occurrence, the clinician may be instructed to image the treatment site to watch for a constriction or protrusion before starting another treatment.

Figure 8:
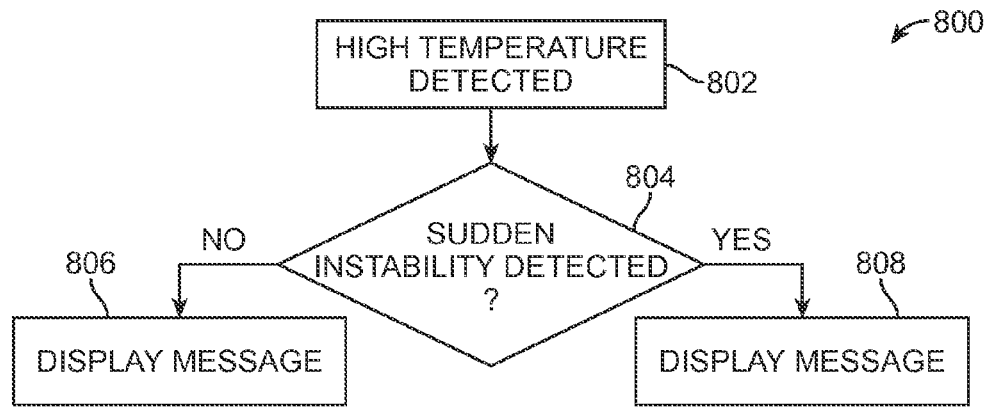
FIG. 8 is a block diagram illustrating an algorithm for providing operator feedback when a high temperature condition is detected in accordance with an embodiment of the technology described herein.

FIG. 8 is a block diagram illustrating an algorithm 800 for providing operator feedback when a high temperature condition is detected in accordance with an embodiment of the technology described herein. In one implementation the algorithm 800 is executed in response to detection of a high temperature condition as shown at operation 802. At operation 804, algorithm 800 evaluates data from the treatment to determine if the high temperature condition involved a situation that included sudden instability or if it did not. Sudden instability can be caused, for example, by sudden unintended movement of the patient or catheter, thereby causing the electrode to be pushed harder (i.e., contact force is increased) into the vessel wall, dislodged from the vessel wall, or moved to another location. In the event that sudden instability is not detected at operation 804, a first message may be displayed or other alert provided to the clinician. This is illustrated by operation 806. The alert can include an indication that a high temperature has been detected and an instruction to image the treatment site to determine if the site has been damaged. In the event that sudden instability is detected, an alternative alert can be provided to the user. This is indicated by operations 804 and 808. The alternative alert can be a message that, in addition to indicating the occurrence of the high temperature and instructing the clinician to image the treatment site, may also indicate the possibility that the electrode may have moved from its original site. Such feedback may prompt the clinician to investigate the situation before continuation treatment, and to take appropriate action as warranted based on the condition.

E. Feedback Related to High Impedance

As with high temperature, the system can also be configured to detect and provide alerts for high impedance conditions. As will be appreciated, impedance to RF current passing from a treatment electrode through the body to a dispersive return electrode can provide an indication of characteristics of the tissue that is in contact with the treatment electrode. For example, an electrode positioned in the blood stream in a renal artery may measure a lower impedance than an electrode contacting the vessel wall. Furthermore, as tissue temperature rises its impedance decreases. However, if the tissue gets too hot it may desiccate and its impedance may increase. During a treatment as tissue is gradually heated it is expected that impedance will decrease. A significant rise in impedance can be a result of an undesired situation such as tissue desiccation or electrode movement. In certain implementations, the system 10 may be configured to cease energy delivery if the real time impedance rise is higher than a predefined maximum change in impedance from the starting impedance.

Figure 9:
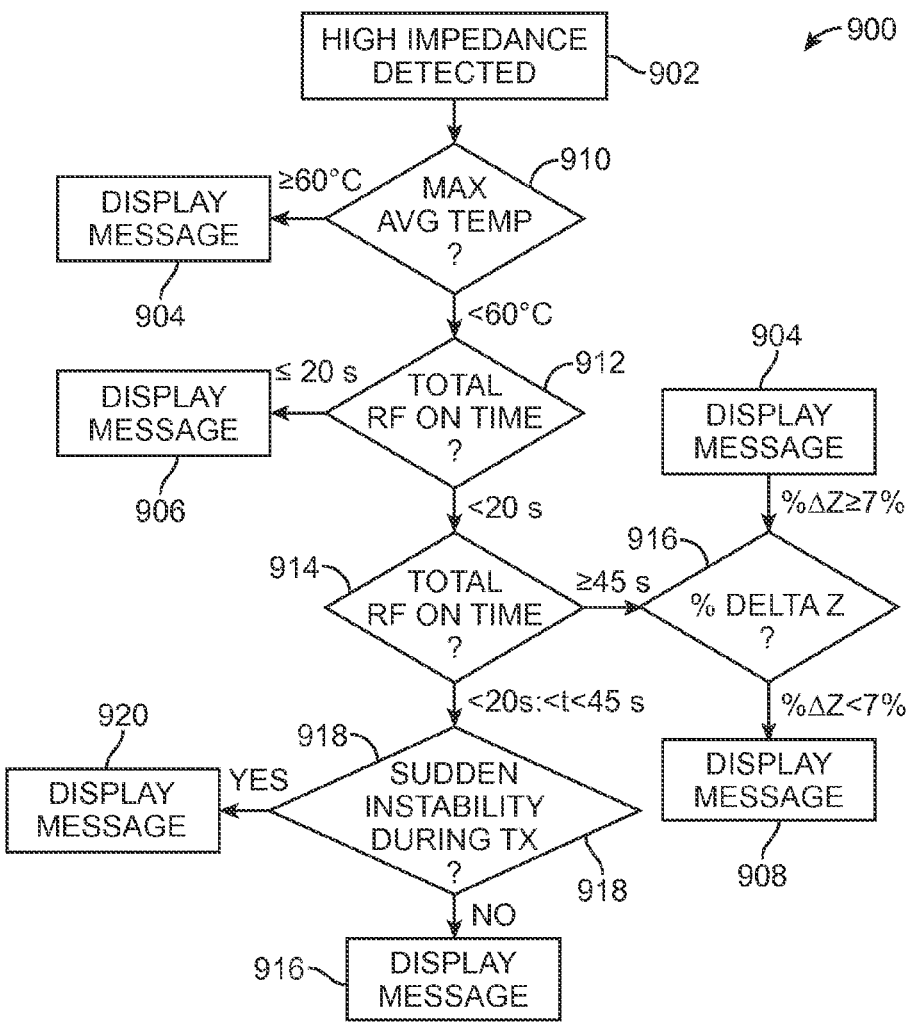
FIG. 9 is an operational flow diagram illustrating an example process for providing operator feedback upon the occurrence of a high impedance condition in accordance with an embodiment of the present technology.

FIG. 9 is an operational flow diagram illustrating an example process for providing operator feedback upon the occurrence of a high impedance condition in accordance with an embodiment of the present technology. In the depicted embodiment, the algorithm 900 evaluates data from the treatment and monitors impedance. Impedance, for example, can be calculated based on the voltage and current delivered to the electrode. If a high-impedance event is detected as illustrated at operation 902, the system proceeds to determine the cause for the high-impedance event. In some embodiments, the system can be configured to evaluate whether (a) tissue temperature was high and desiccation was likely, (b) the electrode moved, or (c) there was poor electrode contact or no electrode contact with the vessel wall. The algorithm 900 evaluates the data to determine which, if any, of these three situations occurred and alerts the clinician accordingly.

In accordance with one embodiment, upon detection of a high impedance (operation 902), the temperature during the treatment is evaluated at operation 910. The system can evaluate average temperature over a determined time period, for example, or the temperature above a baseline integrated over time. If the evaluated temperature is above a certain threshold (e.g., at or above 60° C.) then the high impedance may be attributed to high tissue temperature resulting in desiccation. In this event, at operation 904 a message may be displayed instructing the clinician to check for a constriction or protrusion (i.e., to image the treatment site) and to avoid treating again in the same location. Conversely, if the evaluated temperature is below the threshold (e.g., below 60° C.), the process 900 proceeds to operation 912.

At operation 912, the process 900 evaluates if the high impedance event occurred early in treatment (e.g., in the first 20 seconds of energy delivery) when power is relatively low. If yes, it is unlikely that tissue temperature was high and more likely that the electrode initially had poor or no contact and subsequently established better contact, causing impedance to rise unexpectedly. In this event, at operation 906 a message may be displayed instructing the clinician to attempt to establish better contact and repeat treatment at the same site. However, if the event occurs later in treatment (e.g., more than 20 seconds elapsed), the process 900 proceeds to operation 914.

At operation 914, the process 900 evaluates when the high-impedance event occurred during treatment. For example, if the event occurred after a predetermined period of time (e.g., 45 seconds), when the power has reached high levels, the process 900 proceeds to operation 916. However, if the event occurred when power is being ramped up and is not at its highest (e.g., between 20 seconds and 45 seconds), the algorithm proceeds to operation 918.

At operation 916, the algorithm 900 calculates the percentage change in impedance (% ΔZ) at the time of the high impedance event compared to the impedance at a specified time. This is the period when power is sustained at a high level. In one embodiment, the percentage change in impedance is calculated as:

$$\% \Delta Z = 100 * \left| \frac{[(\text{final } avg\ Z) - (avg\ Z@45\ \text{sec})]}{(avg\ Z@45\ \text{sec})} \right| \quad (1)$$

If % ΔZ is greater than or equal to a predetermined amount (e.g., 7%) then it may be likely that tissue began to desiccate due to high temperature. In this event, at operation 904 a message may be displayed instructing the clinician to check for a constriction or protrusion (i.e., to image the treatment site) and to avoid treating again in the same location. If % ΔZ is less than to a predetermined amount (e.g., 7%), tissue desiccation is less likely and it is more likely that the electrode moved to cause the high impedance event. In this event, at operation 908 may be displayed notifying the clinician that the electrode may have moved. In the event the electrode has moved or may have moved, it is unlikely that tissue temperature reached a high level. Accordingly, it is expected that treating in the same location can be done if there are no or limited other locations to perform another treatment.

At operation 918, the process 900 may determine whether a sudden instability occurred. If such instability was present, it is a possibility that the electrode was unintentionally moved. In this event, at operation 920, a message may be displayed notifying the clinician that the electrode may have moved. As discussed above, the clinician may exhibit caution and avoid treating the original location or the location to which the electrode moved or the clinician may opt to treat in the same location if no other sites or a limited number of sites are available for further treatment. Otherwise, if no sudden instability occurred, it is more likely that the electrode had poor contact. In this event, at operation 916 a message may be displayed instructing the clinician to attempt to establish better contact and that treating the same site is safe.

In some embodiments, temperature and impedance data is taken for a sample time interval (e.g., 20 seconds). At a shorter time interval (e.g., every 1.5 seconds), the standard deviation of the impedance and temperature data is calculated. A first standard temperature for an interval is calculated as the standard deviation of the temperature divided by the standard deviation of the temperature at the initial time interval. If the standard deviation of the impedance measurements is greater than or equal to a pre-determined value (e.g., 10 Ohms), and the first standard temperature is greater than a pre-determined threshold (e.g., 3), then the process 900 can alert the user (e.g., at operation 916, indicating poor electrode contact.) However, if the standard deviation of the impedance measurement is outside the acceptable range, but the first standard temperature is within the acceptable range, at operation 908, a message is displayed to alert the clinician that there is electrode instability.

In accordance with a further embodiment of the process 900, the impedance of two or more electrodes can each provide an independent impedance reading. During delivery of the therapeutic assembly 21 to the treatment site (e.g., within the renal artery), the impedance readings of the electrodes are typically different due to the anatomy of the vasculature, as the catheter 12 will conform to the path of least resistance, often bending at vasculature curves to only contact one wall of the renal artery. In some embodiments, once the therapeutic assembly 21 is in position for treatment, the therapeutic assembly 21 can be expanded circumferentially to contact the entire circumferential surface of a segment of the renal artery wall. This expansion can place multiple electrodes in contact with the renal artery wall. As the therapeutic assembly 21 is expanded into the treatment configuration and the electrodes make increased contact with the renal artery wall, the impedance values of the individual electrodes can increase and/or approach the same value. With good, stable contact, fluctuations of impedance values also reduce as described above. The energy generator 26 can continually or continuously monitor the individual impedance values. The values can then be compared to determine when contact has been effectively made, as an indication of successful treatment. In further embodiments, a moving average of impedance can be compared to a pre-determined range of variability of impedance values with limits set to guide stability measures.

F. Feedback Related to Vasoconstriction

In further embodiments, the system 10 may generate a message related to the occurrence of vasoconstriction. In particular, while treatment is being delivered, blood vessels may contract to a less-than-optimal diameter. Constricted blood vessels can lead to reduced blood flow, increased treatment site temperatures, and increased blood pressure. Vasoconstriction can be measured by sampling the amplitude (the "envelope") of real-time temperature data. The current envelope can be compared to a previous envelope sample taken (e.g., 200 ms prior). If the difference between the current envelope and the previous time point envelope is less than a pre-determined value (e.g., less than −0.5° C., or, in other words, there is a less than a 0.5° C. reduction in the present envelope value compared to the envelope value at the previous time point), then measurements are taken at a future time point (e.g., in 5 seconds). If the difference in average temperature at the future time point and the current time point is more than a given temperature threshold (e.g., more than 1° C.), then an algorithm 1000 may determine that an undesirably high level of constriction exists, and can cease/alter energy delivery. In such an event, the system 10 may generate a message indicating the high constriction condition. However, depending on the circumstances, different actions by the clinician may be appropriate.

Figure 10:
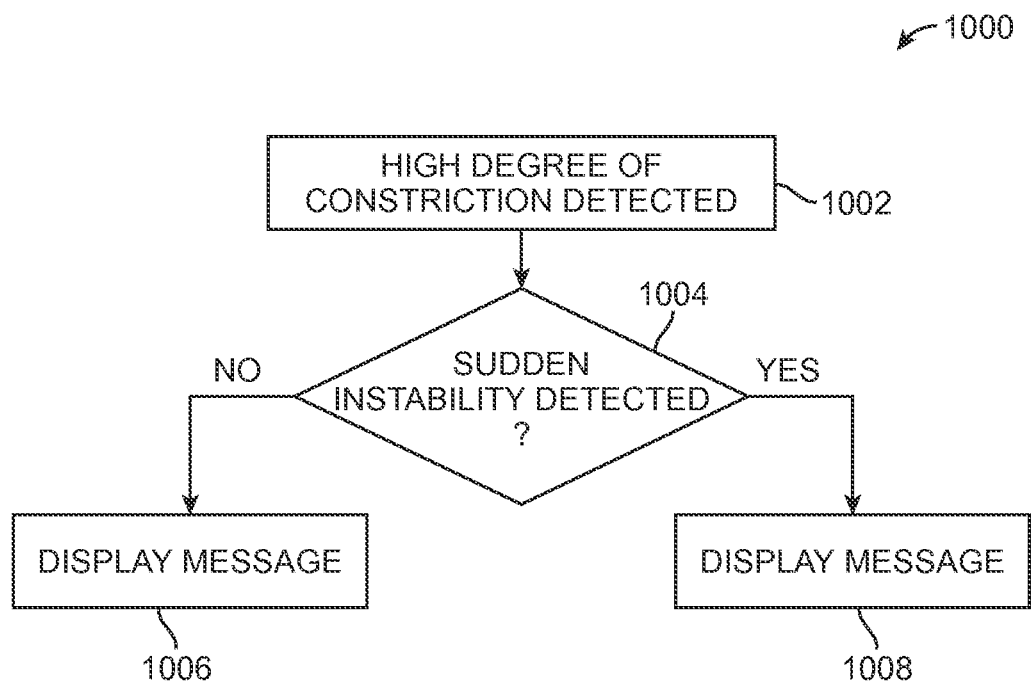
FIG. 10 is a block diagram illustrating a process for providing operator feedback when a high degree of vessel constriction is detected in accordance with an embodiment of the present technology.

FIG. 10 is a block diagram illustrating a process for providing operator feedback when a high degree of vessel constriction is detected in accordance with an embodiment of the present technology. In one embodiment, the process 1000 is executed in response to detection of a high constriction level (e.g., vessels constricted at or below a certain diameter) as illustrated at operation 1002. At operation 1004, the process 1000 evaluates data from the treatment to determine whether or not the high constriction level involved a situation that included sudden instability. An indication of sudden instability can indicate that the electrode has moved.

In the event that sudden instability is not detected, at operation 1006 a message may be displayed indicating that a high constriction level has been detected and an instructing the clinician to reduce treatment power. In further embodiments, the energy level may be automatically altered in response to the detected constriction level. In the event that sudden instability is detected at operation 1004, an alternative message may be displayed as indicated by operation 1008. This alternative message may, in addition to indicating the occurrence of the high constriction level and instructions to the clinician, also indicate the possibility that the electrode may have moved from its original site. Such feedback may prompt the clinician to alter or cease treatment.

G. Feedback Related to Cardiac Factors

1. Feedback Related to Abnormal Heart Rate

Like other physiological conditions mentioned above, in certain circumstances the system 10 may generate a message related to the occurrence of an abnormal heart rate. In particular, while treatment is being delivered, heart rate may exceed or fall below desirable conditions (e.g., temporary procedural or chronic bradycardia). Instantaneous heart rate can be determined by measuring real-time temperature and impedance. More specifically, a real-time temperature reading can be filtered, for example, between 0.5 Hz and 2.5 Hz using a second order Butterworth filter. Local maxima of the filtered signal are determined. The local maxima are the detected peaks of the real-temperature signal. The instantaneous beat rate is the interval between the peaks, as the signal peaks correspond to the periodic change in the cardiac cycle.

In one embodiment, the system 10 may cease/alter energy delivery if the heart rate falls outside of a desirable range. In such an event, the system may generate a message indicating the adverse heart rate condition. However, depending on the circumstances, different actions by the clinician may be appropriate.

Figure 11A:
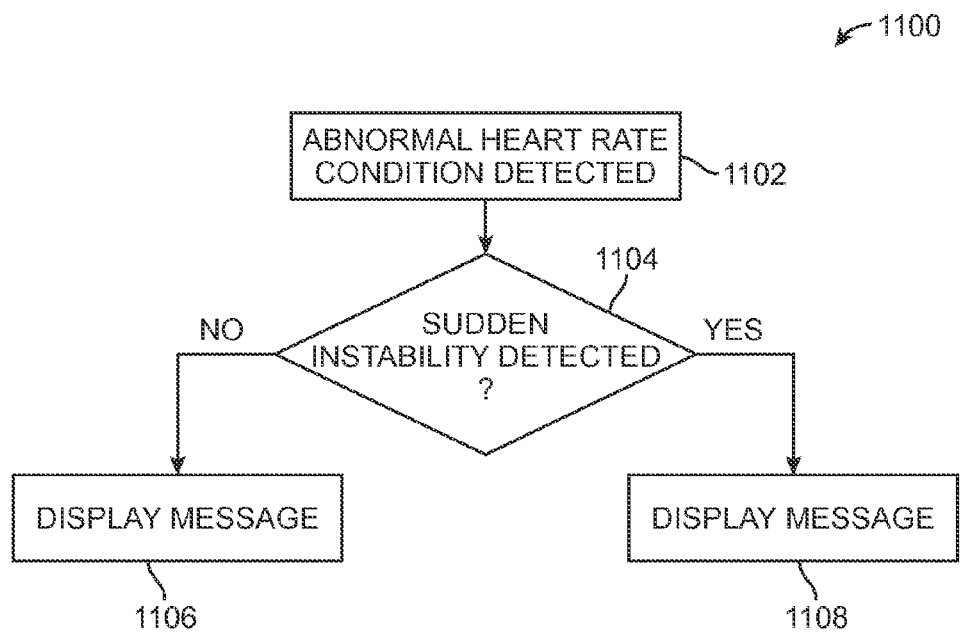
FIG. 11A is a block diagram illustrating an algorithm for providing operator feedback/instructions upon detection of an abnormal heart rate condition in accordance with an embodiment of the present technology.

FIG. 11A is a block diagram illustrating an algorithm 1100 for providing operator feedback/instructions upon detection of an abnormal heart rate condition in accordance with an embodiment of the present technology. In one implementation, for example, at operation 1102, the algorithm 1100 may be executed in response to an abnormal heart rate condition (e.g., above or below a pre-determined threshold). At operation 1104, the algorithm 1100 evaluates data from the treatment to determine if the detected abnormal heart rate condition involved a situation that included sudden instability. An indication of sudden instability can indicate that the electrode moved.

In the event that sudden instability is not detected at operation 1104, a first message may be displayed to the clinician at operation 1106, such as an indication that an abnormal heart rate has been detected and an instruction to the clinician to reduce treatment power. In further embodiments, the energy level may be automatically altered in response to the detected adverse heart rate. In the event that sudden instability is detected at operation 1104, an alternative message may be displayed at operation 1108 that, in addition to indicating the occurrence of the abnormal heart rate and instructions to the clinician, may also indicate the possibility that the electrode may have moved from its original site. Such feedback may prompt the clinician to alter or cease treatment.

2. Feedback Related to Low Blood Flow

The system 10 may also be configured to generate a message related to low blood flow conditions. For example, if blood flow falls below a certain level during treatment (or if vessels are undesirably narrow), the convective heat removed from the electrode and tissue surface is reduced. Excessively high tissue temperatures can lead to the negative outcomes described above, such as thrombosis, charring, unreliable lesion size, etc. Reducing power from the generator 26 to prevent the tissue from reaching an unacceptable temperature can lead to insufficient lesion depth, and nerves may not be heated to sufficient ablation temperatures. An algorithm can be used to measure blood flow or the loss of heat to the blood stream. In one embodiment, blood flow can be measured with a flow meter or a Doppler sensor placed in the renal artery on a separate catheter or on the treatment catheter 12. In another embodiment, heat loss or thermal decay can be measured by delivering energy (e.g., RF energy) to raise a blood, tissue, or substrate temperature. The energy can be turned off and the algorithm can include monitoring the temperature as a gauge of thermal decay. A rapid thermal decay may represent sufficient blood flow, while a gradual thermal decay may represent low blood flow. For example, in one embodiment, the algorithm 1110 can indicate a low blood flow if the slope of real-time temperature measurements over the starting temperature exceeds a preset threshold (e.g., 2.75) and the average temperature is greater than a preset temperature (e.g., 65° C.). In further embodiments, thermal decay and/or blood flow can be characterized by measuring temperature oscillations of an electrode delivering RF or resistive heat. At a given temperature or power delivery amplitude/magnitude, a narrow oscillation range may indicate a relatively low thermal decay/blood flow.

Figure 11B:
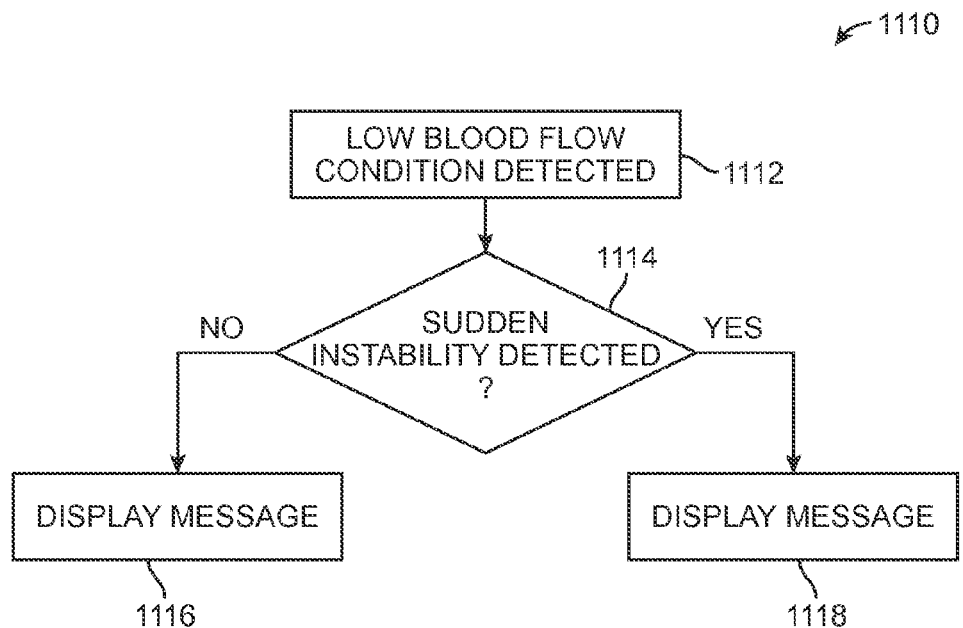
FIG. 11B is a block diagram illustrating an process for providing operator feedback/instructions upon occurrence of a low blood flow condition in accordance with an embodiment of the present technology.

FIG. 11B is a block diagram illustrating an process 1110 for providing operator feedback/instructions upon occurrence of a low blood flow condition in accordance with an embodiment of the present technology. In one implementation, at operation 1112, the process 1110 is executed in response to a detected low blood flow condition (e.g., flow below a pre-determined threshold.) At operation 1114, the process 1110 evaluates data from the treatment to determine if the low blood flow condition involved a situation that included sudden instability. In the event that sudden instability is not detected at operation 1114, a first message may be displayed at operation 1116, such as an indication that low blood flow has been detected and an instruction to a clinician to reduce treatment power. In the event that sudden instability is detected, an alternative message may be displayed at operation 1118, in addition to indicating the occurrence of low blood flow and instructions to the clinician, may also indicate the possibility that the electrode may have moved from its original site. As noted above, such feedback may prompt the clinician to alter or cease treatment.

In further embodiments, if blood flow or thermal decay values are lower than a typical or pre-determined threshold, the energy delivery process 1110 can include automatically altering one or more conditions or characteristics of treatment or of the catheter to improve blood flow. For example, in one embodiment, the process 1110 can respond to a low blood flow by pulsing the energy provided to the electrode rather than providing continuous energy. This may allow the lower blood flow to more adequately remove heat from the tissue surface while still creating a sufficiently deep lesion to ablate a nerve.

In another embodiment, the process 1110 can include responding to a low blood flow by cooling the electrodes, as described in further detail in International Patent Application No. PCT/US2011/033491, filed Apr. 21, 2011, and U.S. patent Application Publication No. 2011-0264011, Ser. No. 12/871,457, filed Aug. 30, 2010.

In a further embodiment, the process 1110 can respond to a low blood flow by requiring a manual increase of blood flow to the region. For example, a non-occlusive balloon can be inflated in the abdominal aorta, thereby increasing pressure and flow in the renal artery. The balloon can be incorporated on the treatment catheter or on a separate catheter.

IV. Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal denervation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 12:
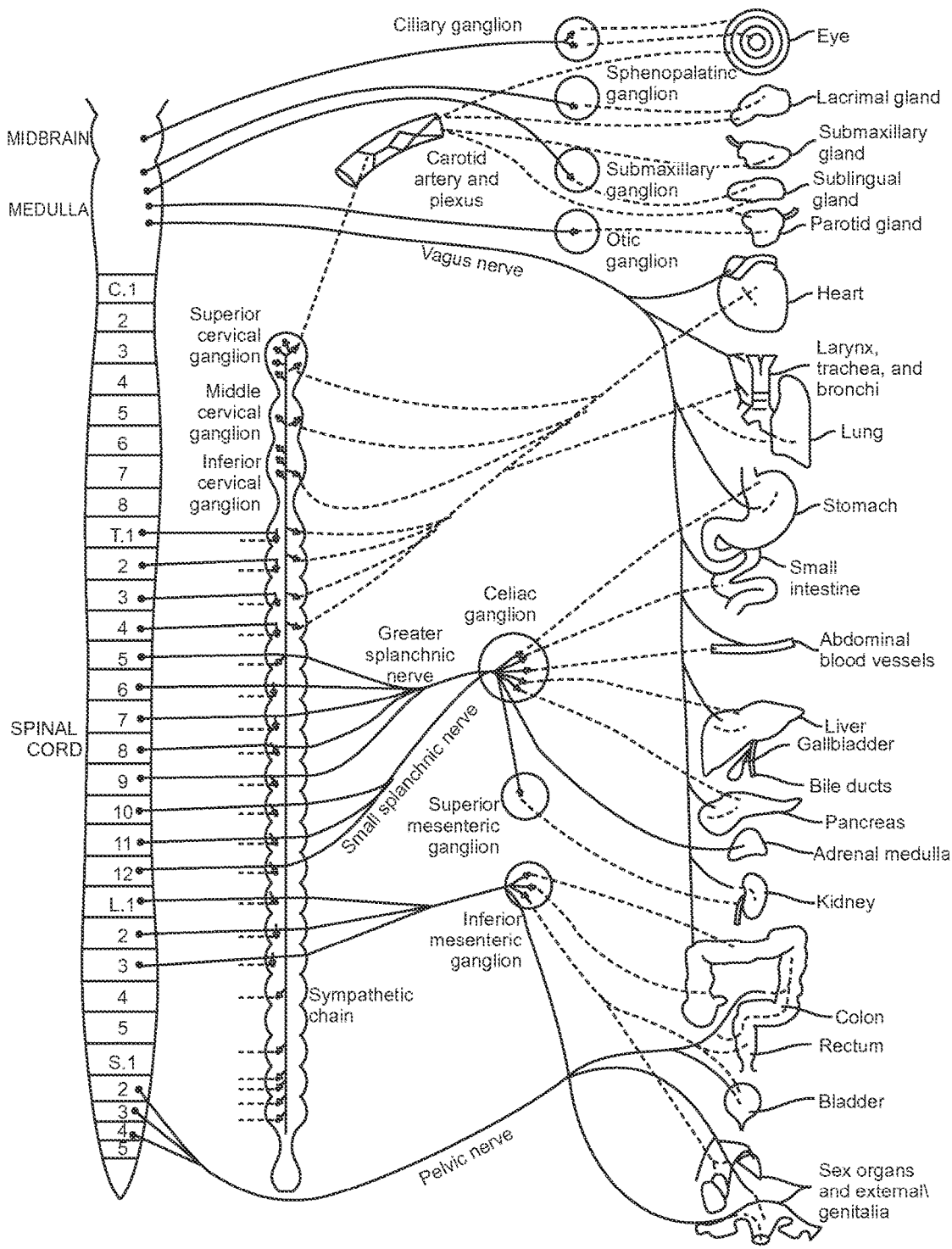
FIG. 12 is a conceptual illustration of the sympathetic nervous system (SNS) and how the brain communicates with the body via the SNS.

As shown in FIG. 12, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 13:
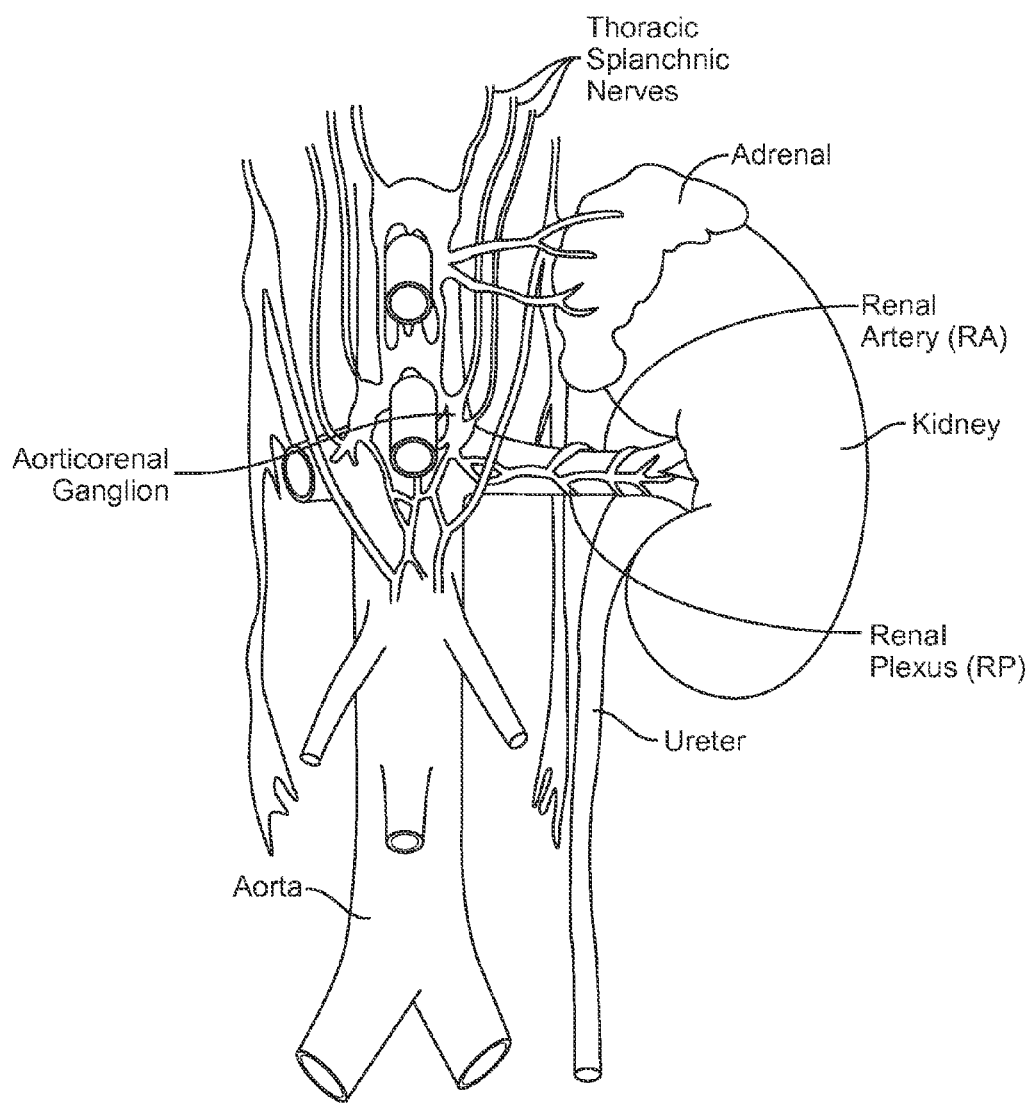
FIG. 13 is an enlarged anatomic view of nerves innervating a left kidney to form the renal plexus surrounding the left renal artery.

As shown in FIG. 13, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 14A:
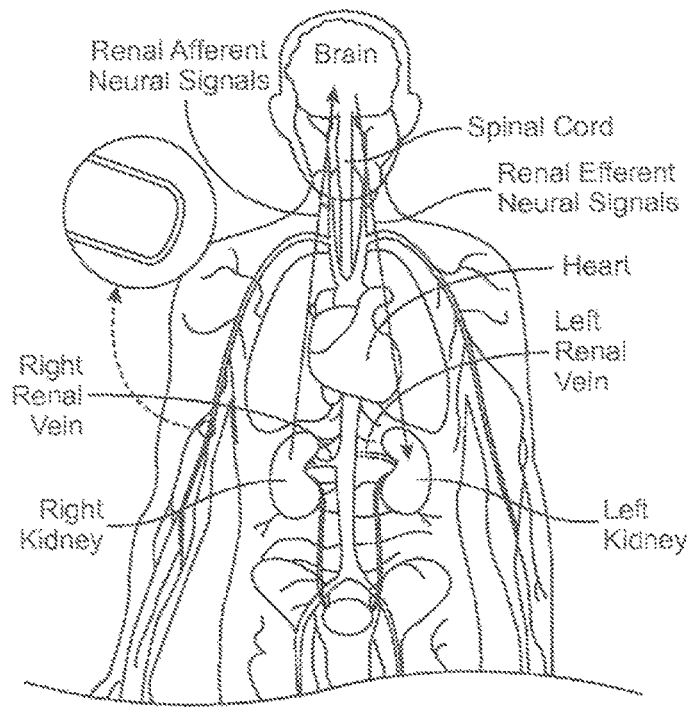
FIG. 14A illustrates an anatomic view of a human body depicting neural efferent and afferent communication between the brain and kidneys.
Figure 14B:
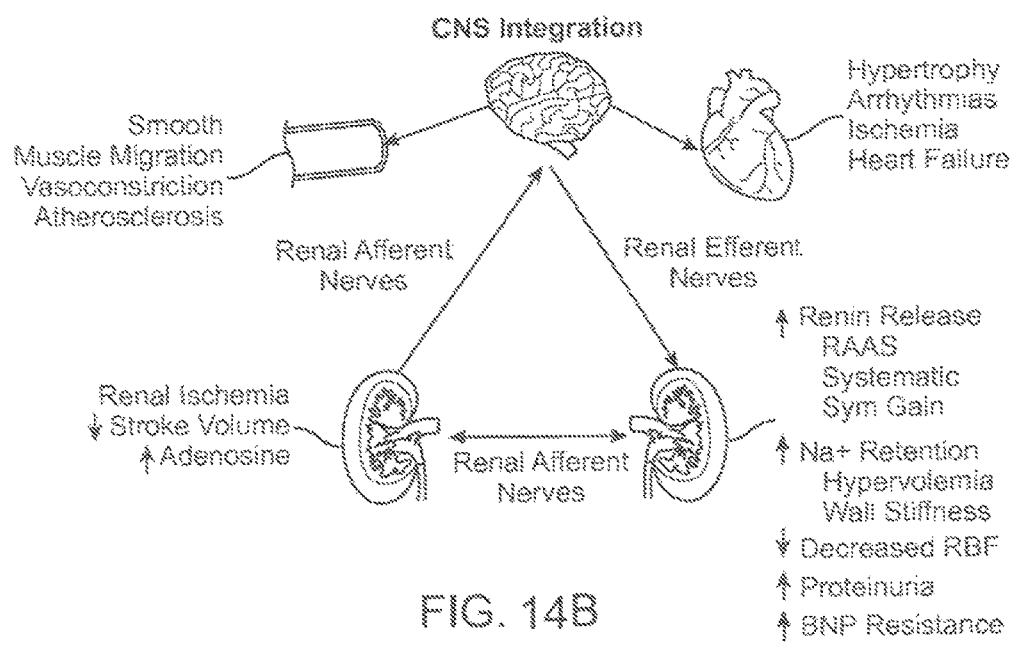
FIG. 14B illustrates a conceptual view of a human body depicting neural efferent and afferent communication between the brain and kidneys.

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 14A and 14B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 12. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 15A:
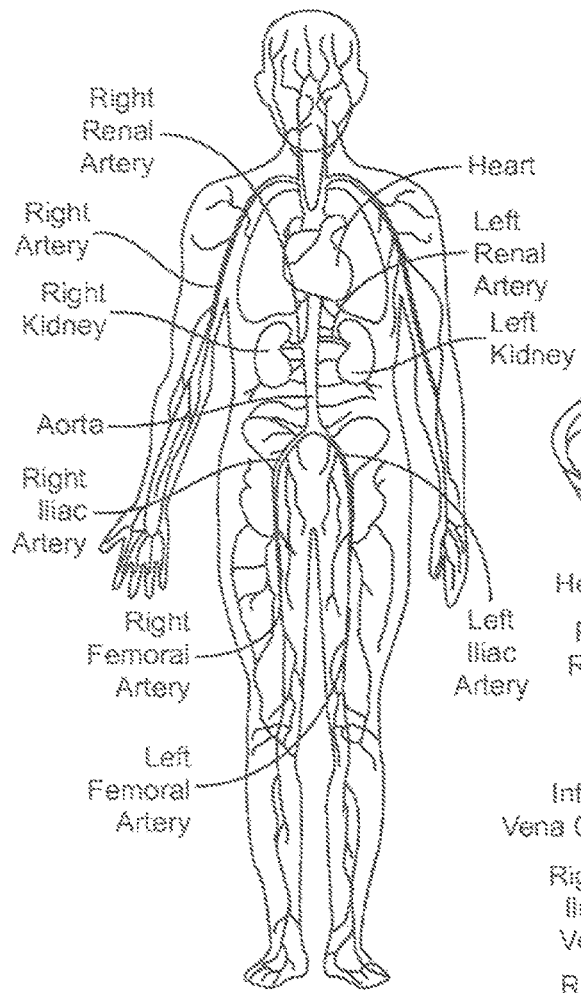
FIG. 15A illustrates an anatomic view of the arterial vasculature of a human.

In accordance with the present technology, neuromodulation of a left and/or right renal plexus (RP), which is intimately associated with a left and/or right renal artery, may be achieved through intravascular access. As FIG. 15A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 15B:
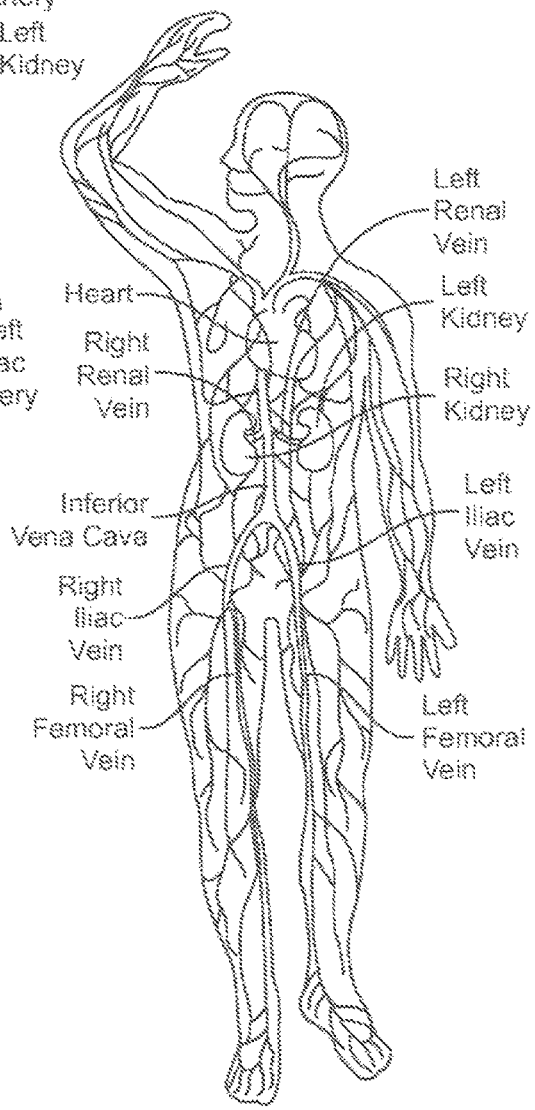
FIG. 15B illustrates an anatomic view of the venous vasculature of a human.

As FIG. 15B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, consistent positioning and appropriate contact force applied by the energy delivery element to the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e., cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the mesh structures described herein and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, DRA, typically is in a range of about 2-10 mm, with most of the patient population having a DRA of about 4 mm to about 8 mm and an average of about 6 mm. Renal artery vessel length, LRA, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

Figure 16:
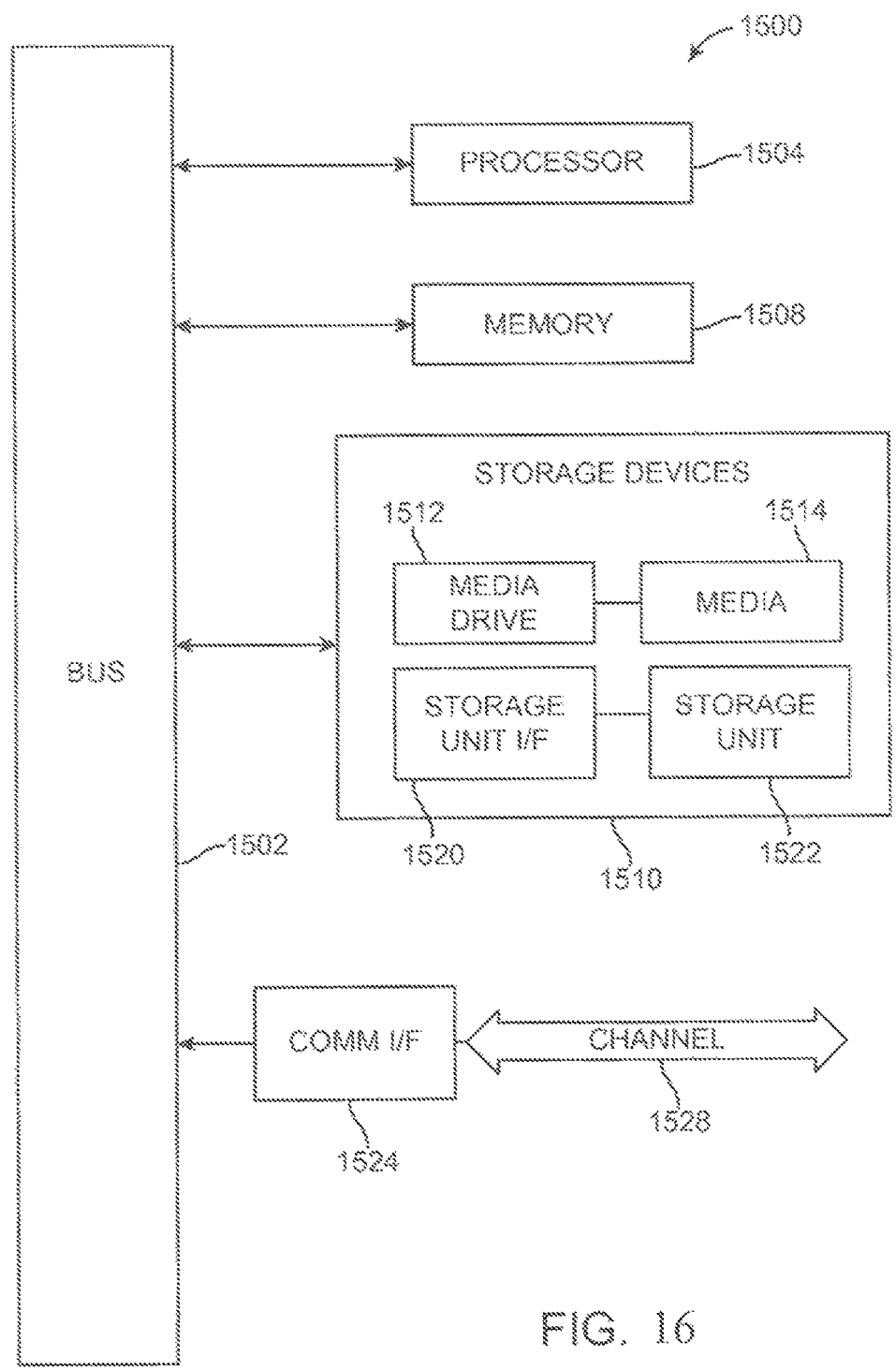
FIG. 16 illustrates an example computing module that may be used to implement various features of the systems and methods disclosed herein.

An additional property of the renal artery that may be of interest is the degree of renal motion relative to the aorta, induced by respiration and/or blood flow pulsatility. A patient's kidney, which located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30 degrees-135 degrees.

Where components or modules of the invention are implemented in whole or in part using software, in one embodiment, these software elements can be implemented to operate with a computing or processing module capable of carrying out the functionality described with respect thereto. One such example computing module is shown in FIG. 16. Various embodiments are described in terms of this example—computing module 1500. After reading this description, it will become apparent to a person skilled in the relevant art how to implement the invention using other computing modules or architectures.

Referring now to FIG. 16, computing module 1500 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 1500 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 1500 might include, for example, one or more processors, controllers, control modules, or other processing devices, such as a processor 1504. Processor 1504 might be implemented using a general-purpose or special-purpose processing engine such as, for example, a microprocessor, controller, or other control logic. In the illustrated example, processor 1504 is connected to a bus 1502, although any communication medium can be used to facilitate interaction with other components of computing module 1500 or to communicate externally.

Computing module 1500 might also include one or more memory modules, simply referred to herein as main memory 1508. For example, preferably random access memory (RAM) or other dynamic memory, might be used for storing information and instructions to be executed by processor 1504. Main memory 1508 might also be used for storing temporary variables or other intermediate information during execution of instructions to be executed by processor 1504. Computing module 1500 might likewise include a read only memory ("ROM") or other static storage device coupled to bus 1502 for storing static information and instructions for processor 1504.

The computing module 1500 might also include one or more various forms of information storage mechanism 1510, which might include, for example, a media drive 1512 and a storage unit interface 1520. The media drive 1512 might include a drive or other mechanism to support fixed or removable storage media 1514. For example, a hard disk drive, a floppy disk drive, a magnetic tape drive, an optical disk drive, a CD or DVD drive (R or RW), or other removable or fixed media drive might be provided. Accordingly, storage media 1514 might include, for example, a hard disk, a floppy disk, magnetic tape, cartridge, optical disk, a CD or DVD, or other fixed or removable medium that is read by, written to or accessed by media drive 1512. As these examples illustrate, the storage media 1514 can include a computer usable storage medium having stored therein computer software or data.

In alternative embodiments, information storage mechanism 1510 might include other similar instrumentalities for allowing computer programs or other instructions or data to be loaded into computing module 1500. Such instrumentalities might include, for example, a fixed or removable storage unit 1522 and an interface 1520. Examples of such storage units 1522 and interfaces 1520 can include a program cartridge and cartridge interface, a removable memory (for example, a flash memory or other removable memory module) and memory slot, a PCMCIA slot and card, and other fixed or removable storage units 1522 and interfaces 1520 that allow software and data to be transferred from the storage unit 1522 to computing module 1500.

Computing module 1500 might also include a communications interface 1524. Communications interface 1524 might be used to allow software and data to be transferred between computing module 1500 and external devices. Examples of communications interface 1524 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1524 might typically be carried on signals, which can be electronic, electromagnetic (which includes optical) or other signals capable of being exchanged by a given communications interface 1524. These signals might be provided to communications interface 1524 via a channel 1528. This channel 1528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 1508, storage unit 1520, media 1514, and channel 1528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 1500 to perform features or functions of the present invention as discussed herein.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method of controlling current delivered to a therapeutic assembly for ablating target tissue adjacent a vessel intima in a patient, the therapeutic assembly being configured for receiving energy via only a single wire and comprising an electrode having a total surface area (TSA), a portion of the TSA being in contact with the vessel intima of the patient and defining an electrode active surface area (ASA), the method comprising:
   determining a desired current density for ablating the target tissue;
   determining a surface area size of the ASA;
   delivering an amount of energy to the therapeutic assembly via the single wire to achieve the desired current density through the ASA;
   during delivery of energy thereto, measuring at the therapeutic assembly one or more treatment parameters selected from temperature, voltage, and current through the electrode; and
   based on at least one of the measured treatment parameters, adjusting the amount of energy delivered to the therapeutic assembly via the single wire as necessary to achieve or maintain the desired current density through the ASA.

2. The method of claim 1, further comprising calculating a power level of the electrode based on the measured parameters of voltage and current, and wherein adjusting the amount of energy delivered to the therapeutic assembly is based on at least one of the measured parameters and the calculated power level.

3. The method of claim 2, wherein adjusting the amount of energy delivered to the therapeutic assembly further comprises increasing or decreasing the amount of energy delivered to the therapeutic assembly to achieve a determined current level through the electrode, wherein the determined current level is determined based on at least one of a change in the temperature of the electrode, a change in impedance of the tissue, and the calculated power of the electrode.

4. The method of claim 3, further comprising determining a maximum increase in current through the electrode by at least one of a maximum current level, a maximum temperature, a maximum power, and a maximum change in impedance of the tissue.

5. The method of claim 4, wherein the step of adjusting the amount of energy delivered to the therapeutic assembly comprises overriding the maximum increase in current through the electrode based on at least one of the temperature, the power, and the impedance measured.

6. The method of claim 1, wherein determining a desired current density for ablating tissue comprises determining a desired current density for a neuromodulation treatment.

7. The method of claim 1, wherein the step of adjusting the amount of energy delivered to the therapeutic assembly comprises limiting the resulting amount of current change to a maximum change in current through the ASA.

8. The method of claim 1, further comprising terminating the energy delivered to the therapeutic assembly based on at least one of a set amount of time, a predetermined temperature value, a predetermined current value, a predetermined integral of current over time value, and a predetermined impedance change value.

9. The method of claim 1, wherein the step of adjusting the amount of energy delivered to the therapeutic assembly comprises monitoring a rate of change in temperature of tissue at the electrode, and if temperature increases faster than a predetermined rate, reducing energy delivered to the therapeutic assembly.

10. The method of claim 1, wherein the step of adjusting the amount of energy delivered to the therapeutic assembly comprises monitoring a rate of change in tissue impedance through a return path of the delivered energy, and if the impedance increases faster than a predetermined rate, reducing the amount of energy delivered to the therapeutic assembly.

11. The method of claim 1, further comprising monitoring patient stability and generating an alert in the event that sudden patient instability is detected.

12. The method of claim 1, further comprising monitoring a treatment criterion and if the criterion is unmet after a predetermined period of time, changing the amount of energy delivered to the therapeutic assembly.

13. The method of claim 1, further comprising monitoring a temperature at the intima and cooling the electrode when the temperature reaches a predetermined threshold.

* * * * *